United States Patent [19]
Iwasawa et al.

[11] Patent Number: 6,048,894
[45] Date of Patent: Apr. 11, 2000

[54] SUBSTITUTED AMIDE DERIVATIVES

[75] Inventors: Yoshikazu Iwasawa; Tetsuya Aoyama; Kumiko Kawakami; Sachie Arai; Toshihiko Satoh; Yoshiaki Monden, all of Tsukuba, Japan

[73] Assignee: Banyu Pharmaceutical Co., Ltd., Tokyo, Japan

[21] Appl. No.: 09/117,533

[22] PCT Filed: Feb. 7, 1997

[86] PCT No.: PCT/JP97/00304

§ 371 Date: Aug. 4, 1998

§ 102(e) Date: Aug. 4, 1998

[87] PCT Pub. No.: WO97/29073

PCT Pub. Date: Aug. 14, 1997

[30] Foreign Application Priority Data

Feb. 7, 1996 [JP] Japan .................................. 8-045502

[51] Int. Cl.[7] .................................................. A61K 31/34
[52] U.S. Cl. ............................................. 514/471; 549/496
[58] Field of Search .............................. 514/471; 549/496

[56] References Cited

U.S. PATENT DOCUMENTS 5,488,149  1/1996  Nomoto et al. ........................ 562/449

FOREIGN PATENT DOCUMENTS

| 7-138214 WO A1 | 5/1995 | Japan . |
| 96/05168 WO A1 | 2/1996 | WIPO . |
| 96/05169 | 2/1996 | WIPO . |

*Primary Examiner*—Amelia Owens
*Attorney, Agent, or Firm*—Oblon, Spivak, McClelland, Maier & Neustadt, P.C.

[57] ABSTRACT

The present invention relates to a compound represented by general formula (I) or a pharmaceutically acceptable salt or ester thereof:

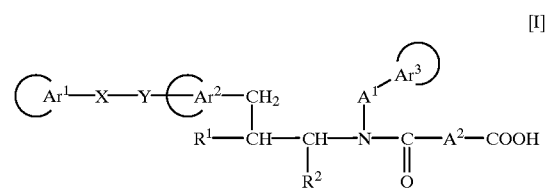

[wherein each of

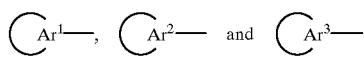

is an aryl group or an aromatic heterocyclic group; $A^1$ is a $C_{1-6}$ chain hydrocarbon group or a group represented by $-A^{1a}-W^1-A^{1b}-$ (wherein $W^1$ is an oxygen atom, a sulfur atom, an ethynylene group, a cyclopropylene group or a group represented by $-NR^W-$); $A^2$ is a $C_{1-8}$ chain hydrocarbon group; $R^1$ is a lower alkyl group, a lower alkenyl group, a lower alkoxy group, a carboxyl group, a lower alkoxycarbonyl group, a carbamoyl group, a lower alkylcarbamoyl group, a group represented by $R^aCOO-$ (wherein $R^a$ is a hydrogen atom, an amino group, a lower alkyl group, a lower alkoxy group or a lower alkylamino group) or by $R^bCONR^c-$ (wherein $R^b$ is a hydrogen atom, an amino group, a lower alkyl group, a lower alkoxy group or a lower alkylamino group) or an alicyclic group; $R^2$ is a lower alkyl group; and each of X and Y is an oxygen atom, a sulfur atom, a carbonyl group, a group represented by $-CHR^d-$ or by $-NR^e-$, or X and Y together represent a vinylene group or an ethynylene group, provided that when one of X and Y is an oxygen atom, a sulfur atom or group represented by $-NR^e-$, the other is a carbonyl group or a group represented by $-CHR^d-$] and an antitumor agent comprising it as an active ingredient.

14 Claims, No Drawings

SUBSTITUTED AMIDE DERIVATIVES

TECHNICAL FIELD

The present invention relates novel substituted amide derivatives. More particularly, the substituted amide derivatives of the present invention inhibit protein-farnesyl transferase (PFT) in vivo thereby to suppress function of oncogene protein Ras and thus present antitumor activities, etc., and they are thus useful in the pharmaceutical field.

BACKGROUND ART

The ras oncogene is activated by mutation, and its translation product Ras protein plays an important role in transformation of normal cells to cancer cells. Such activation of ras oncogene is observed in many cancers such as colorectal cancers or pancreatic cancers, and the proportion thereof is reported to reach about 20% of the total human cancers. Accordingly, it is expected that canceration can be suppressed and antitumor effects can be obtained by suppressing such activation of ras oncogene, by inhibiting the function of Ras protein as its product.

Recently, it has been found that farnesyl-modification of Ras protein itself is essential for function of Ras protein, and it is possible to suppress localization of Ras protein at the plasma membrane by inhibiting this farnesyl-modification and thereby to inhibit transformation to cancer cells. The protein-farnesyl transferase (PFT) is an enzyme which catalyses this farnesyl-modification of Ras protein, and by inhibiting this enzyme, it is possible to suppress function of carcinogenic Ras protein. Further, this enzyme contributes to farnesyl-modification of only very limited proteins in vivo. Accordingly, the inhibitor for such an enzyme is expected to be a safe and highly selective antitumor agent. From such a viewpoint, many PFT inhibitors have been developed in recent years (Cell, vol. 57, pp. 1167–1177 (1989); Proc. Natl. Acad. Sci., vol. 86, pp. 8323–8327 (1989); ditto, vol. 90, pp. 2281–2285 (1993); Science, vol. 245, pp. 379–385 (1989); ditto, vol. 260 pp. 1934–1937 (1993); ditto, vol. 260, pp. 1937–1942 (1993); J. Biol. Chem., vol. 266, pp. 15575–15578 (1991); J. Antibiotics, vol. 46, pp. 222–227 (1993); Natur Medicine, vol. 1, pp. 792–797 (1995); JP-A-5-201869; JP-A-5-213992).

Further, it has recently been found by a research by the present inventors that these PFT inhibitors can block the reactivation of static viruses by suppressing development of matured Ras proteins and are useful as anti-AIDS (HIV) agents (PCT/JP95/02489).

However, up to now, all of the reported PFT inhibitors have had some problems for development as medicines, such that the activities are low in cells, and the effects in vivo are inadequate.

DISCLOSURE OF THE INVENTION

It is an object of the present invention to provide a novel antitumor agent or an anti-AIDS agent which inhibits the protein-farnesyl transferase (PFT) thereby to inhibit functional manifestation of oncogene protein Ras and which thus provides antitumor or anti-AIDS effects.

The present inventors have found that a compound represented by general formula (I) or a pharmaceutically acceptable salt or ester thereof:

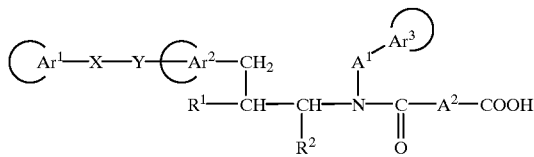

[wherein each of

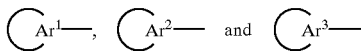

which may be the same or different, is an aryl group or an aromatic heterocyclic group which may have substituent(s) selected from the group consisting of a halogen atom, a hydroxyl group, an amino group, a nitro group, a cyano group, a carboxyl group, a lower alkyl group, a lower alkenyl group, a lower alkoxy group, a lower hydroxyalkyl group, a lower fluoroalkyl group, a lower alkoxycarbonyl group, a carbamoyl group and a lower alkylcarbamoyl group; $A^1$ is a $C_{1-6}$ chain hydrocarbon group which may have substituent(s) selected from the group consisting of a halogen atom, a lower alkyl group, an oxo group, a lower hydroxyalkyl group and a lower alkoxy group or a group represented by $-A^{1a}-W^1-A^{1b}-$ (wherein $A^{1a}$ is a $C_{1-5}$ chain hydrocarbon group which may have substituent(s) selected from the group consisting of a halogen atom, a lower alkyl group, an oxo group, a lower hydroxyalkyl group and a lower alkoxy group; $A^{1b}$ is a single bond or a $C_{1-4}$ chain hydrocarbon group which may have substituent(s) selected from the group consisting of a halogen atom, a lower alkyl group, an oxo group, a lower hydroxyalkyl group and a lower alkoxy group; $W^1$ is an oxygen atom, a sulfur atom, an ethynylene group, a cyclopropylene group or a group represented by $-NR^W-$; and $R^W$ is a hydrogen atom or a lower alkyl group); $A^2$ is a $C_{1-8}$ chain hydrocarbon group which may have substituent(s) selected from the group consisting of a halogen atom, a lower alkyl group, a hydroxyl group, a lower hydroxyalkyl group, a lower alkoxy group, a carboxyl group, a lower alkoxycarbonyl group, a lower alkenyloxycarbonyl group, a lower carboxyalkyl group, an aryl group and an aralkyl group; $R^1$ is a lower alkyl group or a lower alkenyl group which may have substituent(s) selected from the group consisting of a hydroxyl group, a lower alkoxy group, a lower alkoxycarbonyl group, a carbamoyl group, a lower alkylcarbamoyl group and a lower alkylhydrazinocarbonyl group, a lower alkoxy group, a carboxyl group, a lower alkoxycarbonyl group, a carbamoyl group, a lower alkylcarbamoyl group, a group represented by $R^aCOO-$ (wherein $R^a$ is a hydrogen atom, an amino group, a lower alkyl group, a lower alkoxy group or a lower alkylamino group) or by $R^bCONR^c-$ (wherein $R^b$ is a hydrogen atom, an amino group, a lower alkyl group, a lower alkoxy group or a lower alkylamino group; and $R^c$ is a hydrogen atom or a lower alkyl group) or an alicyclic group which may have substituent(s) selected from the group consisting of a halogen atom, a hydroxyl group, an amino group, a nitro group, a cyano group, a carboxyl group, a lower alkyl group, a lower alkenyl group, a lower alkoxy group, a lower hydroxyalkyl group, a lower fluoroalkyl group, a lower alkoxycarbonyl group, a carbamoyl group and a lower alkylcarbamoyl group and may have one or two oxygen atoms and/or one or two nitrogen atoms; $R^2$ is a lower alkyl group; and each of X and Y which may be the same or different, is an oxygen atom, a sulfur atom, a carbonyl group, a group represented by —CHR$^d$— (wherein R$^d$ is a hydrogen atom or a lower alkyl group) or by —NR$^e$— (wherein R$^e$ is a hydrogen atom or a lower alkyl group), or X and Y together represent a vinylene group or an ethynylene group, provided that when one of X and Y is an oxygen atom, a sulfur atom or a group represented by —NR$^3$— (wherein R$^e$ is the same as defined above), the other is a carbonyl group or a group represented by —CHR$^d$— (wherein R$^d$ is the same defined above)], inhibits the protein-farnesyl transferase (PFT) thereby to suppress function of oncogene protein Ras, and thus is useful as an antitumor agent or an anti-AIDS agent. The present invention has been accomplished on the basis of this discovery.

Thus, the present invention relates to a compound of the formula (I), or its pharmaceutically acceptable salt or ester, as well as its application.

Symbols and terms used in this specification will be explained.

The aryl group means a phenyl group, a naphthyl group or an anthryl group. A phenyl group or a naphthyl group is preferred.

The aromatic heterocyclic group means a 5-membered or 6-membered monocyclic aromatic heterocyclic group containing one or two hetero atoms, which are the same or different, selected from the group consisting of an oxygen atom, a nitrogen atom and a sulfur atom, or a fused aromatic heterocyclic group having such a monocyclic aromatic heterocyclic group fused with the above-mentioned aryl group or having the same or different such monocyclic aromatic heterocyclic groups fused with each other, which may, for example, be a pyrrolyl group, an imidazolyl group, a pyrazolyl group, a pyridyl group, a pyrazinyl group, a pyrimidinyl group, a pyridazinyl group, an oxazolyl group, an isoxazolyl group, a furyl group, a thienyl group, a thiazolyl group, an isothiazolyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthylidinyl group, a quinoxalinyl group, a quinazolinyl group, a cinnolinyl group or a pteridinyl group. Among them, a furyl group, a thienyl group, a pyridyl group, a pyrimidinyl group, an oxazolyl group, an isoxazolyl group, a thiazolyl group, a benzofuranyl group, a benzothienyl group, a benzimidazolyl group, a benzoxazolyl group, a benzothiazolyl group or a quinolyl group is preferred.

The halogen atom may be a fluorine atom, a chlorine atom, a bromine atom or an iodine atom. For example, a fluorine atom or a chlorine atom is preferred.

The lower alkyl group means a $C_{1-6}$ linear or branched alkyl group, which may, for example, be a methyl group, an ethyl group, a propyl group, an isopropyl group, a butyl group, a sec-butyl group, a tert-butyl group, a pentyl group or a hexyl group. Among them, a methyl group or an ethyl group is preferred.

The lower alkenyl group means a $C_{2-6}$ linear or branched alkenyl group, such as a vinyl group, an allyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, or a 4-pentenyl group.

The lower alkoxy group means a $C_{1-6}$ alkoxy or alkylenedioxy group, which may, for example, be a methoxy group, an ethoxy group, a propoxy group, an isopropoxy group, a butoxy group, a tert-butoxy group, a methylenedioxy group, an ethylenedioxy group or a trimethylenedioxy group. Among them, a methoxy group, an ethoxy group or a methylenedioxy group is preferred.

The lower hydroxyalkyl group means the above-mentioned lower alkyl group having a hydroxyl group, i.e. a $C_{1-6}$ hydroxyalkyl group, such as a hydroxymethyl group, a hydroxyethyl group, a hydroxypropyl group or a hydroxybutyl group. Among them, a hydroxymethyl group or a hydroxyethyl group is preferred.

The lower fluoroalkyl group means the above-mentioned lower alkyl group having fluorine atom(s), i.e. a $C_{1-6}$ fluoroalkyl group, such as a fluoromethyl group, a difluoromethyl group, a trifluoromethyl group, a 1-fluoroethyl group, a 2-fluoroethyl group, a 2,2,2-trifluoroethyl group or a pentafluoroethyl group.

The lower alkoxycarbonyl group means a $C_{1-7}$ alkoxycarbonyl group, such as a methoxycarbonyl group, an ethoxycarbonyl group, a propoxycarbonyl group, a butoxycarbonyl group, a pentoxycarbonyl group, an isopropoxycarbonyl group, an isobutoxycarbonyl group, a tert-butoxycarbonyl group, an isopentoxycarbonyl group, a neopentoxycarbonyl group, cyclopropoxycarbonyl group, a cyclobutoxycarbonyl group, a cyclopentoxycarbonyl group, a cyclohexyloxycarbonyl group, a 1-methylcyclopropoxycarbonyl group, a 1-methylcyclopentoxycarbonyl group, a 1-methylcyclobutoxycarbonyl group, a 2-methylcyclobutoxycarbonyl group, a 1,1-dimethylpropoxycarbonyl group, a 1,2-dimethylpropoxycarbonyl group, a 1-ethylpropoxycarbonyl group, a 1,2-dimethylcyclopropoxycarbonyl group, a 2,2-dimethylcyclopropoxycarbonyl group, a 2,3-dimethylcyclopropoxycarbonyl group, a 1,2-dimethylcyclobutoxycarbonyl group, a 1,3-dimethylcyclobutoxycarbonyl group, a 2,2-dimethylcyclobutoxycarbonyl group, a 2,3-dimethylcyclobutoxycarbonyl group, a 3,3-dimethylcyclobutoxycarbonyl group, a 2,4-dimethylcyclobutoxycarbonyl group, a 2,3-dimethylcyclopentoxycarbonyl group, a 2,4-dimethylcyclopentoxycrbonyl group or a 2,5-dimethylcyclopentoxycarbonyl group. Among them, a methoxycarbonyl group, an ethoxycarbonyl group, a propoxycarbonyl group, an isopropoxycarbonyl group, a tert-butoxycarbonyl group, a cyclopropoxycarbonyl group, a cyclobutoxycarbonyl group, a cyclopentoxycarbonyl group, a 1-methylcyclopropoxycarbonyl group, a 1-methylcyclopentoxycarbonyl group, a 1-methylcyclobutoxycarbonyl group, a 1,1-dimethylpropoxycarbonyl group or a 1,2-dimethylpropoxycarbonyl group is preferred.

The lower alkylcarbamoyl group means a carbamoyl group mono-substituted or di-substituted by the above-mentioned lower alkyl group, such as a methylcarbamoyl group, an ethylcarbamoyl group, a dimethylcarbamoyl group or a diethylcarbamoyl group.

The chain hydrocarbon group means a linear saturated aliphatic hydrocarbon group, or a linear unsaturated aliphatic hydrocarbon group having one or more, preferably one or two double bonds, at optional positions on the carbon chain.

The saturated aliphatic hydrocarbon group may, for example, be a methylene group, an ethylene group, a trimethylene group, a tetramethylene group, a pentamethylene group, a hexamethylene group, a heptamethylene group or an octamethylene group.

The unsaturated aliphatic hydrocarbon group may, for example, be a vinylene group, a propenylene group, a 1-butenylene group, a 2-butenylene group, a 1,3-butadienylene group, a 1-pentenylene group, a 2-pentenylene group, a 1,3-pentadienylene group, a 1,4-pentadienylene group, a 1-hexenylene group, a 2-hexenylene group, a 3-hexenylene group, a 1,3-hexadienylene group, a 1,4-hexadienylene group, a 1,5-hexadienylene group, a 1,3,5-hexatrienylene group, a 1-heptenylene group, a 2-heptenylene group, a 3-heptenylene group, a 1,3-heptadienylene group, a 1,4-heptadienylene group, a 1,5-heptadienylene group, a 1,6-heptadienylene group, a 1,3,5-heptatrienylene group, a 1-octenylene group, a 2-octenylene group, a 3-octenylene group, a 4-octenylene group, a 1,3-octadienylene group, a 1,4-octadienylene group, a 1,5-octadienylene group, a 1,6-octadienylene group, a 1,7-octadienylene group, a 2,4-octadienylene group, a 2,5-octadienylene group, a 2,6-octadienylene group, a 3,5-octadienylene group, a 1,3,5-octatrienylene group, a 2,4,6-octatrienylene group or a 1,3,5,7-octatetraenylene group.

The lower alkenyloxycarbonyl group means a $C_{3-7}$ alkenyloxycarbonyl group, such as an allyloxycarbonyl group, a 2-butenyloxycarbonyl group, a 1-methyl-2-propenyloxycarbonyl group, a 3-methyl-2-butnyloxycarbonyl group, a 1-cyclobutenyloxycarbonyl group, a 2-cyclobutenyloxycarbonyl group, a 1-cyclopentenyloxycarbonyl group or a 2-cyclopentenyloxycarbonyl group. Among them, an allyloxycarbonyl group or a 1-methyl-2-propenyloxycarbonyl group is preferred.

The lower carboxyalkyl group means the above-mentioned lower alkyl group having a carboxyl group, i.e. a $C_{1-7}$ carboxyalkyl group, such as a carboxymethyl group, a carboxyethyl group, a carboxypropyl group or a carboxybutyl group. Among them, a carboxymethyl group or a carboxyethyl group is preferred.

The aralkyl group means the above-mentioned lower alkyl group having the above-mentioned aryl group, such as a benzyl group, a phenethyl group, a 3-phenylpropyl group, a 1-naphthylmethyl group, a 2-naphthylmethyl group or a 1-(2-naphthyl)ethyl group. Among them, a benzyl group, a phenethyl group or a 2-naphthylmethyl group is preferred.

The lower alkylamino group means an amino group mono-substituted or di-substituted by the above-mentioned lower alkyl group, such as a methylamino group, an ethylamino group, a dimethylamino group or a diethylamino group.

The lower alkylhydrazinocarbonyl group means a hydrazinocarbonyl group mono-substituted or di-substituted by the above-mentioned lower alkyl group, such as a methylhydrazinocarbonyl group, an ethylhydrazinocarbonyl group, a dimethylhydrazinocarbonyl group or a diethylhydrazinocarbonyl group.

The alicyclic group which may contain one or two oxygen atoms and/or one or two nitrogen atoms, means a 3-membered to 7-membered saturated or unsaturated aliphatic carbocyclic group, or a 3-membered to 7-membered saturated or unsaturated aliphatic oxygen-containing heterocyclic group which contains one or two oxygen atoms and/or one or two nitrogen atoms, such as a cyclopropyl group, a cyclobutyl group, a cyclopentyl group, a cyclohexyl group, a cycloheptyl group, an oxiranyl group, an oxetanyl group, an oxolanyl group, an oxanyl group, an oxepanyl group, a 1,3-dioxetanyl group, a 1,3-dioxolanyl group, a 1,3-dioxanyl group, a 1,4-dioxolanyl group, a 1,3-dioxepanyl group, a 1,4-dioxepanyl group, a cyclobutenyl group, a cyclopentenyl group, a cyclohexenyl group, a cycloheptenyl group, an oxirenyl group, an oxetyl group, a 2,3-dihydrofuranyl group, a 2,5-dihydrofuranyl group, a 3,4-dihydropyranyl group, a 5,6-dihydropyranyl group, a 2,3-dihydrooxepinyl group, a 4,5-dihydrooxepinyl group, a 2,5-dihydrooxepinyl group, a cyclopentadienyl group, a 1,3-cyclohexadienyl group, a 1,4-cyclohexadienyl group, a 2H-pyranyl group, a 4H-pyranyl group, a 2,3,4,5-tetrahydrooxepinyl group, a 2,3,4,7-tetrahydrooxepinyl group, 2,3,6,7-tetrahydrooxepinyl group, a 1,3-dioxorenyl group, a 1,3-dioxinyl group, a 1,4-dioxinyl group, a dihydro-1,4-dioxinyl group, a 6,7-dihydro-1,3-dioxepinyl group, a 4,7-dihydro-1,3-dioxepinyl group, a 5,6-dihydro-1,4-dioxepinyl group, a 2,3-dihydro-1,4-dioxepinyl group, a 1,3-dioxepinyl group, a 1,4-dioxepinyl group, an aziridinyl group, an azetidinyl group, an azolidinyl group, a perhydroazinyl group, a 1,3-diazolidinyl group, a perhydro-1,3-diazinyl group, a perhydro-1,4-diazinyl group, a 3,4-dihydro-2H-azolyl group, a 2,3-dihydro-1H-azolyl group, a 3,4,5,6-tetrahydro-1,3-diazinyl group, a 1,2,5,6-tetrahydro-1,3-diazinyl group, a 1,2,3,4-tetrahydro-1,4-diazinyl group, a 1,4-dihydro-1,4-diazinyl group, a 1,3-oxazolidinyl group, a 4,5-dihydro-1,3-oxazolyl group, a perhydro-1,3-oxazinyl group, a perhydro-1,4-oxazinyl group, a 4,5-dihydro-6H-1,3-oxazinyl group, a 5,6-dihydro-2H-1,3-oxazinyl group, a 3,4-dihydro-2H-1,3-oxazinyl group, a 2,3-dihydro-6H-1,4-oxazinyl group or a 5,6-dihydro-4H-1,4-oxazinyl group.

The salt of the compound of the formula (I) may be a pharmaceutically acceptable common salt, which may, for example, be a base-addition salt of a carboxyl group, or an acid-addition salt of an amino group when the compound has such an amino group, or of a basic heteroaromatic ring when the compound has such a basic aromatic heterocyclic ring.

The base-addition salt may, for example, be an alkali metal salt such as a sodium salt or a potassium salt; an alkaline earth metal salt such as a calcium salt or a magnesium salt; an ammonium salt; or an organic amine salt such as a trimethylamine salt, a triethylamine salt, a dicyclohexylamine salt, an ethanolamine salt, a diethanolamine salt, a triethanolamine salt, a procaine salt or an N,N'-dibenzylethylenediamine salt.

The acid-addition salt may, for example, be an inorganic acid salt such as a hydrochloride, a sulfate, a nitrate, a phosphate or a perchlorate; an organic acid salt such as a maleate, a fumarate, a tartrate, a citrate, an ascorbate or a trifluoroacetate; or a sulfonate such as a methanesulfonate, an isethionate, a benzenesulfonate or a p-toluenesulfonate.

The ester of the compound of the formula (I) means a pharmaceutically acceptable common ester of a carboxyl group adjacent to $A^2$, of a carboxyl group if such a carboxyl group or a lower carboxyalkyl group is present on the chain hydrocarbon group as $A^2$, of a carboxyl group as $R^1$, or of a carboxyl group if such a carboxy group is present on the group represented by

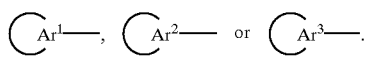

It may, for example, be an ester with a lower alkyl group such as a methyl group, an ethyl group, a propyl group, an isopropyl group, a butyl group, a sec-buryl group, a tert-butyl group, a pentyl group, an isopentyl group, a neopentyl group, a cyclopropyl group, a cyclobutyl group or a cyclopentyl group, an ester with an aralkyl group such as a benzyl group or a phenethyl group, an ester with a lower alkenyl group such as an allyl group or a 2-butenyl group, an ester with a lower alkoxylalkyl group such as a methoxymethyl group, a 2-methoxyethyl group or a 2-ethoxyethyl group, an ester with a lower alkanoyloxyalkyl group such as an acetoxymethyl group, a pivaloyloxymethyl group or a 1-pivaloyloxyethyl group, an ester with a lower alkoxycarbonylalkyl group such as a methoxycarbonylmethyl group or an isopropoxycarbonylmethyl group, an ester with a lower carboxylalkyl group such as a carboxymethyl group, an ester with a lower alkoxycarbonyloxyalkyl group such as a 1-(ethoxycarbonyloxy)ethyl group or a 1-(cyclohexyloxycarbonyloxy)ethyl group, an ester with a lower carbamoyloxyalkyl group such as a carbamoyloxymethyl group, an ester with a phthalidyl group, or an ester with a (5-substituted-2-oxo-1,3-dioxol-4-yl)methyl group such as a (5-methyl-2-oxo-1,3-dioxol-4-yl)methyl group.

Further, when a hydroxyl group is present at the γ- or δ-position of the terminal carboxyl group or of a carboxyl group when such a carboxyl group or a lower carboxylalkyl group is present on the chain hydrocarbon group represented by $A^2$, such a hydroxyl group and a carboxyl group may form an intramolecular ester i.e. a 5-membered or 6-membered lactone ring.

Further, the compound of the present invention may have stereoisomers such as optical isomers, diastereomers or geometrical isomers, depending upon the form of its substituents. The compound of the present invention includes all of such stereoisomers and their mixtures. Among them, a compound represented by general formula I'-1):

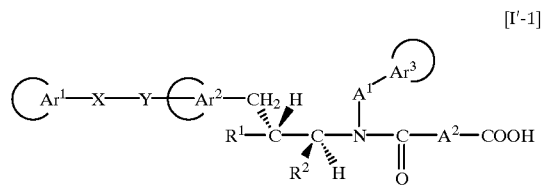

or general formula (I'-2):

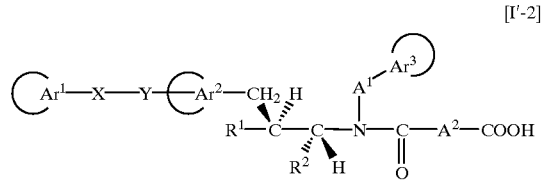

[wherein

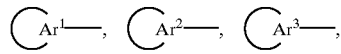

$A^1$, $A^2$, $R^1$, $R^2$, x and y are as defined above] is preferred. Each of

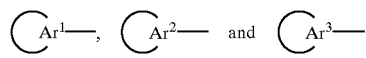

which may be the same or different, means an aryl group or an aromatic heterocyclic group which may have substituent(s) selected from the group consisting of a halogen atom, a hydroxyl group, an amino group, a nitro group, a cyano group, a carboxyl group, a lower alkyl group, a lower alkenyl group, a lower alkoxy group, a lower hydroxyalkyl group, a lower fluoroalkyl group, a lower alkoxycarbonyl group, a carbamoyl group and a lower alkylcarbamoyl group.

The aryl group or the aromatic heterocyclic group which may have substituent(s) selected from the group consisting of a halogen atom, a hydroxyl group, an amino group, a nitro group, a cyano group, a carboxyl group, a lower alkyl group, a lower alkenyl group, a lower alkoxy group, a lower hydroxyalkyl group, a lower fluoroalkyl group, a lower alkoxycarbonyl group, a carbamoyl group and a lower alkylcarbamoyl group, means the above-mentioned aryl group or the above-mentioned aromatic heterocyclic group which is unsubstituted, or the above-mentioned aryl group or the above-mentioned aromatic heterocyclic group which has substituent(s) at optional position(s) for substitution, and said substituent(s) may be one or more, preferably one or two, which may be the same or different and which are selected from the group consisting of a halogen atom, a hydroxyl group, an amino group, a nitro group, a cyano group, a carboxyl group, a lower alkyl group, a lower alkenyl group, a lower alkoxy group, a lower hydroxyalkyl group, a lower fluoroalkyl group, a lower alkoxycarbonyl group, a carbamoyl group and a lower alkylcarbamoyl group.

Among the compounds represented by general formula (I), compounds wherein

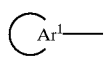

is a phenyl group or a thienyl group, compounds wherein

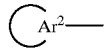

is a phenyl group, a thienyl group, a furyl group, a thiazolyl group, an oxazolyl group, an isoxazolyl group, a pyridyl group or a pyrimidinyl group and compounds wherein

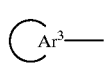

is a phenyl group, a thienyl group, a naphthyl group, a benzothienyl group or a benzofuranyl group, are preferred.

$A^1$ is a $C_{1-6}$ chain hydrocarbon group which may have substituent(s) selected from the group consisting of a halogen atom, a lower alkyl group, an oxo group, a lower hydroxyalkyl group and a lower alkoxy group or a group represented by $—A^{1a}—W^1—A^{1b}—$ (wherein $A^{1a}$ is a $C_{1-5}$ chain hydrocarbon group which may have substituent(s) selected from the group consisting of a halogen atom, a lower alkyl group, an oxo group, a lower hydroxyalkyl group and a lower alkoxy group; $A^{1b}$ is a single bond or a $C_{1-4}$ chain hydrocarbon group which may have substituent(s) selected from the group consisting of a halogen atom, a lower alkyl group, an oxo group, a lower hydroxyalkyl group and a lower alkoxy group; $W^1$ is an oxygen atom, a sulfur atom, an ethynylene group, a cyclopropylene group or a group represented by $—NR^W—$; and $R^W$ is a hydrogen atom or a lower alkyl group).

The $C_{1-6}$ chain hydrocarbon group which may have substituent(s) selected from the group consisting of a halogen atom, a lower alkyl group, an oxo group, a lower hydroxyalkyl group and a lower alkoxy group, means the above-mentioned chain hydrocarbon group having from 1 to 6 carbon atoms, which is unsubstituted, or the above-mentioned chain hydrocarbon group having from 1 to 6 carbon atoms, which has substituent(s) at optional position(s) for substitution, and said substituent(s) may be one or more, preferably from one to three, which are the same or different and which are selected from the group consisting of a halogen atom, a lower alkyl group, an oxo group, a lower hydroxyalkyl group and a lower alkoxy group.

$A^{1a}$ means a $C_{1-5}$ chain hydrocarbon group which may have substituent(s) selected from the group consisting of a halogen atom, a lower alkyl group, an oxo group, a lower hydroxyalkyl group and a lower alkoxy group.

The $C_{1-5}$ chain hydrocarbon group which may have substituent(s) selected from the group consisting of a halogen atom, a lower alkyl group, an oxo group, a lower hydroxyalkyl group and a lower alkoxy group, means the above-mentioned chain hydrocarbon group having from 1 to 5 carbon atoms, which is unsubstituted, or the above-mentioned chain hydrocarbon group having from 1 to 5 carbon atoms, which has substituent(s) at optional position(s) for substitution, and the substituent(s) may be one or more, preferably from one to three, which are the same or different and which are selected from the group consisting of a halogen atom, a lower alkyl group, an oxo group, a lower hydroxyalkyl group and a lower alkoxy group.

$A^{1b}$ is a single bond or a $C_{1-4}$ chain hydrocarbon group which may have substituent(s) selected from the group consisting of a halogen atom, a lower alkyl group, an oxo group, a lower hydroxyalkyl group and a lower alkoxy group.

The $C_{1-4}$ chain hydrocarbon group which may have substituent(s) selected from the group consisting of a halogen atom, a lower alkyl group, an oxo group, a lower hydroxyalkyl group and a lower alkoxy group, means the above-mentioned chain hydrocarbon group having from 1 to 4 carbon atoms, which is unsubstituted, or the above-mentioned chain hydrocarbon group have from 1 to 4 carbon atoms, which has substituent(s) at optional position(s) for substitution, and the substituent(s) may be one or more, preferably from 1 to 3, which are the same or different and which are selected from the group consisting of a halogen atom, a lower alkyl group, an oxo group, a lower hydroxyalkyl group and a lower alkoxy group.

$W^1$ is an oxygen atom, a sulfur atom, an ethynylene group, a cyclopropylene group or a group represented by —$NR^W$—, and preferably an oxygen atom, an ethynylene group or a group represented by —$NR^W$—.

$R^W$ is a hydrogen atom or a lower alkyl group, and preferably a hydrogen atom.

As $A^1$, for example, a group represented by —$CH_2$—, —$CH_2CH_2CH_2$—, —$CH_2CH=CH$—, —$CH_2CH_2O$— or —$CH_2C\equiv C$— is preferred.

$A^2$ means a $C_{1-8}$ chain hydrocarbon group which may have substituent(s) selected from the group consisting of a halogen atom, a lower alkyl group, a hydroxyl group, a lower hydroxyalkyl group, a lower alkoxy group, a carboxyl group, a lower alkoxycarbonyl group, a lower alkenyloxycarbonyl group, a lower carboxyalkyl group, an aryl group and an aralkyl group.

The $C_{1-8}$ chain hydrocarbon group which may have substituent(s) selected from the group consisting of a halogen atom, a lower alkyl group, a hydroxyl group, a lower hydroxyalkyl group, a lower alkoxy group, a carboxyl group, a lower alkoxycarbonyl group, a lower alkenyloxycarbonyl group, a lower carboxyalkyl group, an aryl group and an aralkyl group, means the above-mentioned chain hydrocarbon group having from 1 to 8 carbon atoms, which is unsubstituted, or the above-mentioned chain hydrocarbon group having from 1 to 8 carbon atoms, which has substituent(s) at optional position(s) for substitution, and the substituent(s) may be one or more, preferably from 1 to 3, which are the same or different and which are selected from the group consisting of a halogen atom, a lower alkyl group, a hydroxyl group, a lower hydroxyalkyl group, a lower alkoxy group, a carboxyl group, a lower alkoxycarbonyl group, a lower alkenyloxycarbonyl group, a lower carboxyalkyl group, an aryl group and an aralkyl group.

Compounds wherein $A^2$ is a group represented by formula (a):

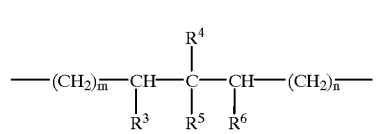

[a]

(wherein $R^3$ is a hydrogen atom, a hydroxyl group, a lower hydroxyalkyl group, a lower alkoxy group or a carboxyl group; $R^4$ is a hydrogen atom, a halogen atom, a hydroxyl group, a lower alkoxy group, a carboxyl group or a lower carboxyalkyl group; $R^5$ is a hydrogen atom, a lower hydroxyalkyl group, a carboxyl group, a lower alkoxycarbonyl group or a lower alkenyloxycarbonyl group; $R^6$ is a hydrogen atom, a halogen atom, a hydroxyl group or a carboxyl group; and each of m and n which may be the same or different is an integer of from 0 to 2) and compounds wherein $A^2$ is a group represented by formula (b):

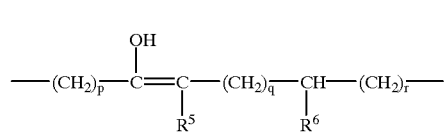

[b]

(wherein $R^5$ is a hydrogen atom, a lower hydroxyalkyl group, a carboxyl group, a lower alkoxycarbonyl group or a lower alkenyloxycarbonyl group; $R^6$ is a hydrogen atom, a hydroxyl group or a carboxyl group; p is 0 or 1; and each of q and r which are the same or different is an integer of from 0 to 2) are preferred.

When $A^2$ is represented by formula (a), $R^3$ is preferably a hydrogen atom, a hydroxyl group or a carboxyl group, $R^4$ is preferably a carboxyl group or a lower carboxyalkyl group such as a carboxymethyl group, $R^5$ and $R^6$ are preferably hydrogen atoms or carboxyl groups, and each of m and n which are the same or different is preferably 0 or 1.

When $A^2$ is represented by formula (b), $R^5$ is a lower hydroxyalkyl group such as a hydroxymethyl group, a carboxyl group, a lower alkoxycarbonyl group such as an ethoxycarbonyl group or a lower alkenyloxycarbonyl group such as an allyloxycarbonyl group, $R^6$ is preferably a hydrogen atom, and p, q and r are preferably 0.

Further, it is well known that in the case of a compound having a partial structure represented by formula (b), there exist enol form and keto form tautomers, as shown below. The compound of the present invention includes such enol form and keto form isomers and their mixtures.

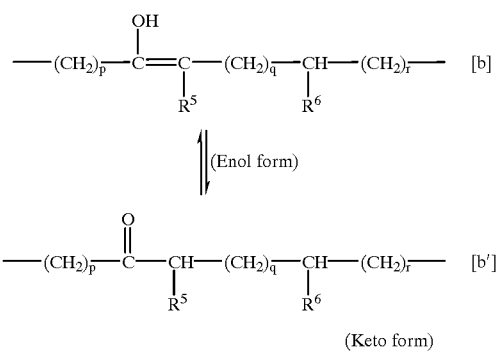

(wherein $R^5$, $R^6$, p, q and r are the same as defined above).

$R^1$ is a lower alkyl group or a lower alkenyl group which may have substituent(s) selected from the group consisting of a hydroxyl group, a lower alkoxy group, a lower alkoxycarbonyl group, a carbamoyl group, a lower alkylcarbamoyl group and a lower alkylhydrazinocarbonyl group, a lower alkoxy group, a carboxyl group, a lower alkoxycarbonyl group, a carbamoyl group, a lower alkylcarbamoyl group, a group represented by $R^aCOO$— (wherein $R^a$ is a hydrogen atom, an amino group, a lower alkyl group, a lower alkoxy group or a lower alkylamino group) or by $R^bCONR^c$— (wherein $R^b$ is a hydrogen atom, an amino group, a lower alkyl group, a lower alkoxy group or a lower alkylamino group; and $R^c$ is a hydrogen atom or a lower alkyl group) or an alicyclic group which may have substituent(s) selected from the group consisting of a halogen atom, a hydroxyl group, an amino group, a nitro group, a cyano group, a carboxyl group, a lower alkyl group, a lower alkenyl group, a lower alkoxy group, a lower hydroxyalkyl group, a lower fluoroalkyl group, a lower alkoxycarbonyl group, a carbamoyl group and a lower alkylcarbamoyl group and may have one or two oxygen atoms and/or one or two nitrogen atoms.

The lower alkyl group or the lower alkenyl group which may have substituent(s) selected from the group consisting of a hydroxyl group, a lower alkoxy group, a lower alkoxycarbonyl group, a carbamoyl group and a lower alkylcarbamoyl group means the above-mentioned lower alkyl group or the above-mentioned lower alkenyl group, which is unsubstituted, or the above-mentioned lower alkyl group or the above-mentioned lower alkenyl group, which has substituent(s) at optional position(s) for substitution, and said substituent(s) may be one or more, preferably one or two, which are the same or different, and which are selected from the group consisting of a hydroxyl group, a lower alkoxy group, a lower alkoxycarbonyl group a carbamoyl group and a lower alkylcarbamoyl group.

The alicyclic group which may have substituent(s) selected from the group consisting of a halogen atom, a hydroxyl group, an amino group, a nitro group, a cyano group, a carboxyl group, a lower alkyl group, a lower alkenyl group, a lower alkoxy group, a lower hydroxyalkyl group, a lower fluoroalkyl group, a lower alkoxycarbonyl group, a carbamoyl group and a lower alkylcarbamoyl group and may have one or two oxygen atoms and/or one or two nitrogen atoms means the above-mentioned alicyclic group which may have one or two oxygen atoms and/or one or two nitrogen atoms and is unsubstituted, or the above-mentioned alicyclic group which may have one or two oxygen atoms and/or one or two nitrogen atoms and has substituent(s) at optional position(s) for substation, and said substituent(s) may be one or more, preferably one or two which are the same or different and which are selected from the group consisting of a halogen atom, a hydroxyl group, an amino group, a nitro group, a cyano group, a carboxyl group, a lower alkyl group, a lower alkenyl group, a lower alkoxy group, a lower hydroxyalkyl group, a lower fluoroalkyl group, a lower alkoxycarbonyl group, a carbamoyl group and a lower alkylcarbamoyl.

As $R^1$, a lower alkoxycarbonyl group such as an ethoxycarbonyl group is preferred.

$R^2$ means a lower alkyl group, but a methyl group, an ethyl group or a propyl group is preferred. Particularly, a methyl group or an ethyl group is preferred.

The group represented by

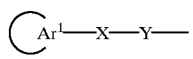

can be present as a substituent at any optional position for substitution on the group represented by the formula

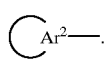

Each of X and Y which are the same or different, is an oxygen atom, a sulfur atom, a carbonyl group, a group represented by —$CHR^d$— (wherein $R^d$ is a hydrogen atom or a lower alkyl group) or by —$NR^e$— (wherein $R^e$ a hydrogen atom or a lower alkyl group), or X and Y together represent a vinylene group or an ethynylene group. When one of X and Y is an oxygen atom, a sulfur atom or a group represented by —$NR^e$— (wherein $R^e$ is the same as defined above), the other is a carbonyl group or a group represented by —$CHR^d$— (wherein $R^d$ is the same as defined above).

Among the compounds represented by general formula (I), compounds wherein X is a group represented by —$NR^e$— (wherein $R^e$ is the same as defined above), and Y is a carbonyl group, compounds wherein X is an oxygen atom, and Y is a group represented by —$CHR^d$— (wherein $R^d$ is the same as defined above), compounds wherein X is a group represented by —$CHR^d$— (wherein $R^d$ is the same as defined above), and Y is an oxygen atom, compounds wherein both X and Y are groups represented by —$CHR^d$— (wherein $R^d$ is the same as defined above) or compounds wherein X and Y together represent a vinylene group are preferred.

Now, processes for producing the compound of the present invention will be described.

The compound represented by general formula (I) of the present invention can be prepared, for example, by the following process 1, 2, 3, 4, 5 6 or 7.

Process 1

A compound represented by general formula (I) can be prepared by reacting a compound represented by general formula (II):

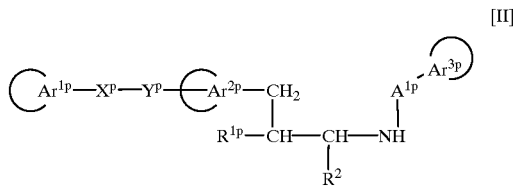

[II]

[wherein each of

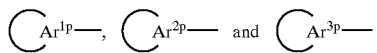, 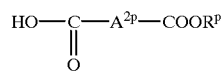 and which are the same or different, is an aryl group or an aromatic heterocyclic group which may have substituent(s) selected from the group consisting of a halogen atom, a nitro group, a cyano group, a lower alkyl group, a lower alkenyl group, a lower alkoxy group, a lower fluoroalkyl group, a lower alkoxycarbonyl group, a carbamoyl group and a lower alkylcarbamoyl group, and a hydroxyl group, an amino group, a carboxyl group and a lower hydroxyalkyl group which may be protected; $A^{1p}$ is a $C_{-6}$ chain hydrocarbon group which may have substituent(s) selected from the group consisting of a halogen atom, a lower alkyl group, an oxo group, a lower hydroxyalkyl group which may be protected and a lower alkoxy group or a group represented by $—A^{1ap}—W^{1p}—A^{1bp}—$ (wherein $A^{1ap}$ is a $C_{1-5}$ chain hydrocarbon group which may have substituent(s) selected from the group consisting of a halogen atom, a lower alkyl group, an oxo group, a lower hydroxyalkyl group which may be protected and a lower alkoxy group; $A^{1bp}$ is a single bond r a $C_{1-4}$ chain hydrocarbon group which may have substituent(s) selected from the group consisting of a halogen atom, a lower alkyl group, an oxo group, a lower hydroxyalkyl group which may be protected and a lower alkoxy group; $W^{1p}$ is an oxygen atom, a sulfur atom, an ethynylene group, a cyclopropylene group or a group represented by $—NR^{Wp}—$; and $R^{Wp}$ is a hydrogen atom, a lower alkyl group or a protecting group for an imino group); $R^{1p}$ is a lower alkyl group or a lower alkenyl group which may have substituent(s) selected from the group consisting of a hydroxyl group which may be protected, a lower alkoxy group, a lower alkoxycarbonyl group, a carbamoyl group, a lower alkylcarbamoyl group and a lower alkylhydrazinocarbonyl group, a lower alkoxy group, a carboxyl group which may be protected, a lower alkoxycarbonyl group, a carbamoyl group, a lower alkylcarbamoyl group, a group represented by $R^aCOO—$ (wherein $R^a$ is a hydrogen atom an amino group, a lower alkyl group, a lower alkoxy group or a lower alkylamino group) or by $R^bCONR^c—$ (wherein $R^b$ is a hydrogen atom, an amino group, a lower alkyl group, a lower alkoxy group or a lower alkylamino group; and $R^c$ is a hydrogen atom or a lower alkyl group) or an alicyclic group which may have substituent(s) selected from the group consisting of a halogen atom, a nitro group, a cyano group, a lower alkyl group, a lower alkenyl group, a lower alkoxy group, a lower fluoroalkyl group, a lower alkoxycarbonyl group, a carbamoyl group and a lower alkylcarbamoyl group and a hydroxyl group, an amino group, a carboxyl group and a lower hydroxyalkyl group which may be protected, and may have one or two oxygen atoms and/or one or two nitrogen atoms; $R^2$ is a lower alkyl group; and each of $X^p$ and $Y^p$ which are the same or different, is an oxygen atom, a sulfur atom, a carbonyl group, a group represented by $—CHR^d—$ (wherein $R^d$ is a hydrogen atom or a lower alkyl group) or by $—NR^{ep}—$ (wherein $R^{ep}$ is a hydrogen atom, a lower alkyl group or a protecting group for an imino group), or $X^p$ or $Y^p$ together represent a vinylene group or an ethynylene group, provided that when one of $X^p$ and $Y^p$ is an oxygen atom, a sulfur atom or a group represented by $—NR^{ep}—$ (wherein $R^{ep}$ is the same as defined above), the other is a carbonyl group or a group represented by $—CHR^d—$ (wherein $R^d$ is the same as defined above)] with a carboxylic acid represented by general formula (III) or its reactive derivative:

$$HO—\underset{\underset{O}{\|}}{C}—A^{2p}—COOR^p \quad [III]$$

[wherein $A^{2p}$ is a $C_{1-8}$ chain hydrocarbon group which may have substituent(s) selected from the group consisting of a halogen atom, a lower alkyl group, a lower alkoxy group, a lower alkoxycarbonyl group, a lower alkenyloxycarbonyl group, an aryl group and an aralkyl group, and a hydroxyl group, a lower hydroxyalkyl group, a carboxyl group and a lower carboxyalkyl group which may be protected; and $R^p$ is a hydrogen atom or a protecting group for a carboxyl group], to obtain a compound represented by general formula (IV):

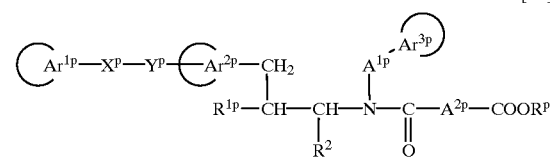

[wherein

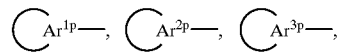

$A^{1p}$, $A^{2p}$, $R^{1p}$, $R^2$, $R^p$, $X^p$ and $Y^p$ are the same as defined above], and, if necessary, removing any protecting groups.

As the reactive derivative of the carboxylic acid represented by general formula (III), an acid halide, a mixed acid anhydride, an active ester or an active amide may, for example, be used.

When the carboxylic acid represented by general formula (III) is used, it is preferred to conduct the reaction in the presence of a condensing agent such as N,N'-dicyclohexylcarbodiimide, 1-ethyl-3-(3-dimethylaminopropyl)carbodiimide or 2-chloro-1,3-dimethylimidazolyl chloride.

The reaction of the compound represented by general formula (II) with the carboxylic acid represented by general formula (III) or its reactive derivative, is conducted usually by using 1 mol or an excess molar amount, preferably from 1 to 5 mols, of the carboxylic acid represented by general formula (III) or its reactive derivative, per mol of the compound represented by general formula (II).

The reaction is conducted usually in an inert solvent. The inert solvent may, for example, be a halogenated hydrocarbon such as methylene chloride, chloroform, carbon tetrachloride, dichloroethane or trichloroethylene; an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide, or a mixture of such solvents.

The reaction temperature is usually from −70° C. to the boiling point of the solvent used for the reaction, preferably from −20° C. to 100° C.

The reaction time is usually from 5 minutes to 7 days, preferably from 10 minutes to 24 hours.

The above reaction can be conducted in the presence of a base to facilitate the reaction.

As such a base, it is preferred to conduct the reaction in the presence of an inorganic base such as sodium hydroxide, potassium hydroxide, calcium hydroxide, sodium carbonate, potassium carbonate or sodium hydrogencarbonate, or an organic base such as triethylamine, N-ethyldiisopropylamine, pyridine, 4-dimethylaminopyridine or N,N-dimethylaniline.

Such a base is used usually in an amount of 1 mol or an excess molar amount, preferably from 1 to 5 mols, per mol of the reactive derivative of the carboxylic acid represented by general formula (III).

The acid halide of the compound represented by general formula (III) can be obtained by reacting the carboxylic acid represented by general formula (III) with a halogenating agent in accordance with a conventional method. As the halogenating agent, thionyl chloride, phosphorus trichloride, phosphorus pentachloride, phosphorus oxychloride, phosphorus tribromide, oxalyl chloride or phosgene may, for example, be used.

The mixed acid anhydride of the compound represented by general formula (III) can be obtained by reacting the carboxylic acid represented by general formula (III) with an alkyl chlorocarbonate such as ethyl chlorocarbonate or with an aliphatic carboxylic acid chloride such as acetyl chloride, in accordance with a conventional method. Further, an intramolecular acid anhydride may be formed between carboxyl groups at both terminals, or when a carboxyl group is present on the chain hydrocarbon group represented as $A^{2p}$ in general formula (III), an intramolecular acid anhydride may be formed between such a carboxyl group and a carboxyl group to be involved in the reaction, to constitute a reactive derivative of the carboxylic acid.

The active ester of the compound represented by general formula (III) can be prepared by reacting the carboxylic acid represented by general formula (III) with an N-hydroxy compound such as N-hydroxysuccinimide, N-hydroxyphthalimide or 1-hydroxybenzotriazole; or a phenol compound such as a 4-nitrophenol, 2,4-dinitrophenol, 2,4,5-trichlorophenol or pentachlorophenol, in the presence of a condensing agent such as N,N'-dicyclohexylcarbodiimide or 1-ethyl-3-(3-dimethylaminopropyl)carbodiimide in accordance with a conventional method.

The active amide of the compound represented by general formula (III) can be prepared by reacting the carboxylic acid represented by general formula (III) with e.g. 1,1'-carbonyldiimidazole or 1,1'-carbonylbis(2-methylimidazole) in accordance with a conventional method.

In the above reaction, when a hydroxyl group, an amino group, an imino group or a carboxyl group which will not be involved in the reaction, is present in a reactant, it is preferred to conduct the reaction after protecting such a hydroxyl group, an amino group, an imino group or a carboxyl group appropriately by a hydroxyl-protecting group, an amino- or imino-protecting group or a carboxyl-protecting group and remove the protecting group after the reaction.

The hydroxyl-protecting group may, for example, be a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a p-nitrobenzyl group or a trityl group; or an acyl group such as a formyl group or an acetyl group. Particularly preferred is a methoxymethyl group, a tetrahydropyranyl group, a trityl group, a tert-butyldimethylsilyl group or an acetyl group.

The amino- or imino-protecting group may, for example, be an aralkylidene group such as a benzylidene group, a p-chlorobenzylidene group or a p-nitrobenzylidene group; an aralkyl group such as a benzyl group, a p-methoxybenzyl group, a p-nitrobenzyl group, a benzhydryl group or a trityl group; a lower alkanoyl group such as a formyl group, an acetyl group, a propionyl group, a butyryl group or a pivaloyl group; a lower haloalkanoyl group such as a trifluoroacetyl group; a lower alkoxycarbonyl group such as a methoxycarbonyl group, an ethoxycarbonyl group, a propoxycarbonyl group or a tert-butoxycarbonyl group; a lower haloalkoxycarbonyl group such as a 2,2,2-trichloroethoxycarbonyl group; an alkenyloxycarbonyl group such as a 2-propenyloxycarbonyl group; an aralkyloxycarbonyl group such as a benzyloxycarbonyl group or a p-nitrobenzyloxycarbonyl group; or a lower alkylsilyl group such as a trimethylsilyl group or a tert-butyldimethylsilyl group. Particularly preferred is an acetyl group, a trifluoroacetyl group, a tert-butoxycarbonyl group or a benzyloxycarbonyl group.

The carboxyl-protecting group may, for example, be a lower alkyl group such as a methyl group, an ethyl group, a propyl group, an isopropyl group or a tert-butyl group; a lower haloalkyl group such as a 2,2,2-trichloroethyl group; a lower alkenyl group such as 2-propenyl group; or an aralkyl group such as a benzyl group, a p-methoxybenzyl group, a p-nitrobenzyl group, a benzhydryl group or trityl group. Particularly preferred is a methyl group, an ethyl group, a tert-butyl group, a 2-propenyl group, a benzyl group, a p-methoxybenzyl group or a benzhydryl group.

After completion of the reaction, conventional treatment is conducted to obtain a crude product of the compound represented by general formula (IV). The compound represented by general formula (IV) may or may not be purified in accordance with a conventional method, and if necessary, reactions for removing protecting groups for a hydroxyl group, an amino group and a carboxyl group may be carried out in a proper combination to obtain a compound represented by general formula (I).

Removal of protecting groups may vary depending upon their types, but can be conducted in accordance with the methods disclosed in a literature [Protective Groups in Organic Synthesis, T. W. Greene, John Wiley & Sons (1981)] or methods similar thereto, for example by solvolysis employing an acid or a base, by chemical reduction employing a metal hydride complex or by catalytic reduction employing a palladium-carbon catalyst or Raney nickel.

Process 2

A compound represented by general formula (I-a):

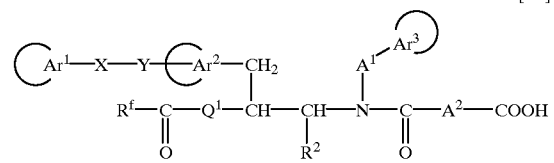

[wherein

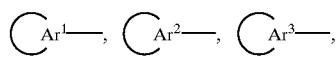

$A^1$, $A^2$, $R^2$, X and Y are the same as defined above, $Q^1$ is an oxygen atom or $-NR^{eq}-$; and $R^f$ is a hydrogen atom, an amino group, a lower alkyl group, a lower alkoxy group or a lower alkylamino group] can be prepared by reacting a compound represented by general formula (V):

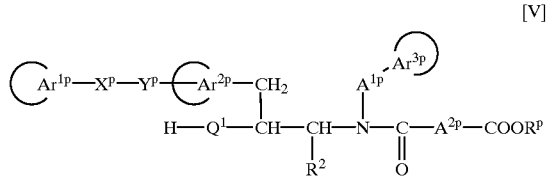

[V]

[wherein

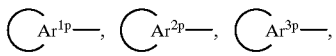

$A^{1p}$, $A^{2p}$, $Q^1$, $R^2$, $R^p$, $X^p$ and $Y^p$ are the same as defined above] with a compound represented by general formula (VI):

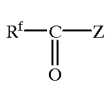

(VI)

[wherein $R^f$ is the same as defined above; and Z is a leaving group] to obtain a compound represented by general formula (IV-a):

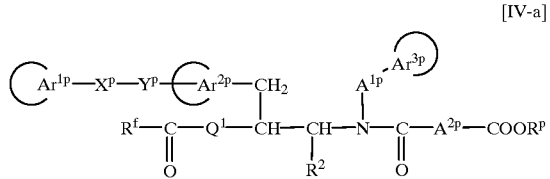

[IV-a]

[wherein

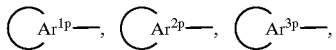

$A^{1p}$, $A^{2p}$, $Q^1$, $R^2$, $R^f$, $R^p$, $X^p$ and $Y^p$ are the same as defined above], and if necessary, removing any protecting group.

Process 2 is a process for preparing a compound represented by general formula (I) of the present invention wherein $R^1$ is a group represented by

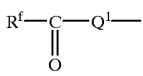

(wherein $Q^1$ and $R^f$ are the same as defined above), i.e. a compound represented by general formula (I-a).

The reaction of the compound represented by general formula (V) with the compound represented by general formula (VI) is conducted usually by using 1 mol or an excess molar amount, preferably from 1 to 3 mols, of the compound represented by general formula (VI) per mol of the compound represented by general formula (V).

The reaction is conducted usually in an inert solvent. The inert solvent may, for example, be a halogenated hydrocarbon such as methylene chloride, chloroform, carbon tetrachloride, dichloroethane or trichloroethylene; an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide, or a mixture of such solvents.

The reaction temperature is usually from −70° C. to the boiling point of the solvent used for the reaction, preferably from −20° C. to 100° C.

The reaction time is usually from 5 minutes to 7 days, preferably from 10 minutes to 24 hours.

The above reaction is preferably conducted in the presence of a base to facilitate the reaction. Especially, unless $Q^1$ in general formula (V) is a group represented by —$NR^{eq}$—, it is essential to conduct the reaction in the presence of an inorganic base such as sodium hydride, n-butyllithium, sodium hydroxide, potassium hydroxide, calcium hydroxide, sodium carbonate, potassium carbonate or sodium hydrogencarbonate, or an organic base such as triethylamine, N-ethyldiisopropylamine, pyridine, 4-dimethylaminopyridine or N,N-dimethylaniline.

Such a base is used usually in an amount of 1 mol or an excess molar amount, preferably from 1 to 5 mols, per mol of the compound represented by general formula (VI).

The leaving group represented by Z in general formula (VI) may, for example, be a halogen atom such as a chlorine atom, a bromine atom or an iodine atom, or an organic sulfonyloxy group such as a methanesulfonyloxy group, a p-toluenesulfonyloxy group for a benzenesulfonyloxy group.

In the above reaction, when a hydroxyl group, an amino group or a carboxyl group which will not be involved in the reaction is present in a reactant, it is preferred to carry out the reaction after protecting such a hydroxyl group, an amino group or a carboxyl group appropriately by a hydroxyl-protecting group, an amino-protecting group or a carboxyl-protecting group, and remove any protecting group after the reaction.

The hydroxyl-protecting group, the amino-protecting group and the carboxyl-protecting group may be the protecting groups mentioned above with respect to process 1.

After completion of the reaction, conventional treatment may be carried out to obtain a crude product of the compound represented by general formula (IV-a). The compound represented by general formula (IV-a) thus obtained may or may not be purified by a conventional method, and if necessary, reactions for removing hydroxyl-, amino- and carboxyl-protecting groups may be carried out in a proper combination to obtain a compound represented by general formula (I-a).

The method for removing a protecting group varies depending upon the type of the protecting group and the stability of the desired compound (I-a). However, removal of protecting groups can be suitably conducted in accordance with the methods disclosed in the above-mentioned literature or methods similar thereto.

Further, a compound represented by general formula (I) wherein $R^1$ is a lower alkoxy group can be prepared by similarly reacting a compound represented by general formula (V) wherein $Q^1$ is an oxygen atom with a compound represented by general formula $R^{fa}$—Z [wherein $R^{fa}$ is a lower alkyl group; and Z is the same as defined above] instead of a compound represented by general formula (VI).

Process 3

A compound represented by general formula (I-b):

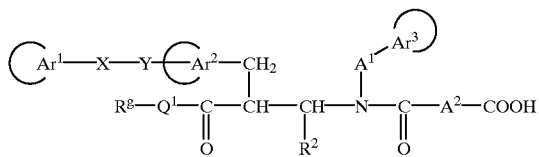

[I-b]

[wherein

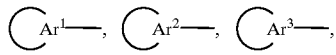

$A^1, A^2, Q^1, R^2$, X and Y are the same as defined above; and $R^g$ is a hydrogen atom or a lower alkyl group] can be prepared by reacting a compound represented by general formula (VII):

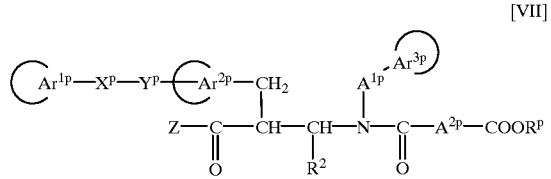

[VII]

[wherein

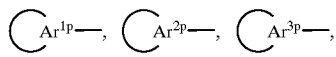

$A^{1p}, A^{2p}, R^2, R^p, X^p, Y^p$ and Z are the same as defined above] with a compound represented by general formula (VIII):

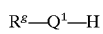 (VIII)

[wherein $R^g$ and $Q^1$ are the same as defined above] to obtain a compound represented by general formula (IV-b):

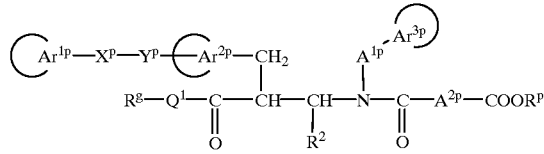

[IV-b]

[wherein

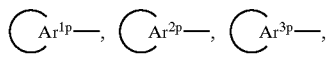

$A^{1p}, A^{2p}, Q^1, R^2, R^g, R^p, X^p$ any $Y^p$ are the same as defined above], and, if necessary, removing any protecting group.

Process 3 is a process for producing a compound represented by general formula (I) of the present invention wherein $R^1$ is a group represented by:

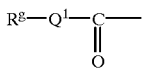

(wherein $Q^1$ and $R^g$ is the same as defined above), i.e. a compound represented by general formula (I-b).

The process is usually carried out in an inert solvent, preferably in the presence of a base, by using 1 mol or an excess molar amount, preferably from 1 to 3 mols, of the compound represented by general formula (VIII), per mol of the compound represented by (VII). With respect to the inert solvent, the base and the reaction conditions, those described above for process 2 can be employed. Accordingly, the reaction and post-treatment are preferably carried out in accordance with process 2.

Process 4

A compound represented by general formula (I-c):

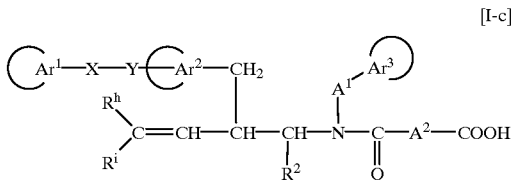

[I-c]

[wherein

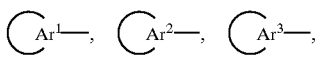

$A^1, A^2, R^2$, X and Y are the same as defined above; $R^h$ is a hydrogen atom or a lower alkyl group; and $R^i$ is a hydrogen atom, a lower alkyl group, a lower alkoxy group, a lower alkoxycarbonyl group, a carbamoyl group, a lower alkylcarbamoyl group or a lower alkylhydrazinocarbonyl group] can be prepared by reacting a compound represented by general formula (IX):

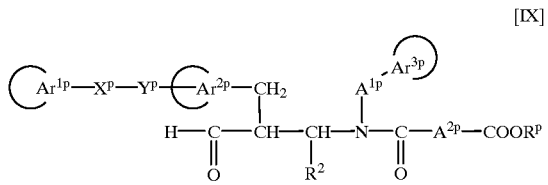

[IX]

[wherein

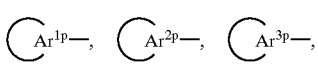

$A^{1p}, A^{2p}, R^2, R^p, X^p$ and $Y^p$ are the same as defined above] with a compound represented by general formula (X):

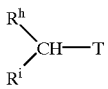

[X]

[wherein $R^h$ and $R^i$ are the same as defined above; and T is a triphenylphosphonio group, a dimethoxyphosphoryl group or a diethoxyphosphoryl group], to obtain a compound represented by general formula (IV-c):

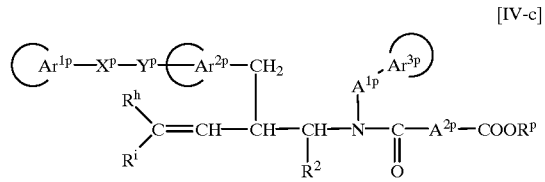

[IV-c]

[wherein

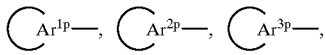

$A^{1p}$, $A^{2p}$, $R^2$, $R^h$, $R^i$, $R^p$, $X^p$ and $Y^p$ are the same as defined above], and if necessary, removing any protecting group.

Process 4 is a process for producing a compound represented by general formula (I) of the present invention wherein $R^1$ is a group represented by:

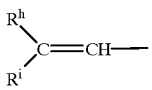

(wherein $R^h$ and $R^i$ are the same as defined above), i.e. a compound represented by general formula (I-c).

The reaction of a compound represented by general formula (IX) with a compound represented by general formula (X) is carried out usually by employing equimolar amounts of the two reactants or using a slightly excess amount of one of them The reaction is carried out usually in an inert solvent. Such an inert solvent may, for example, be an ether such as ethyl ether, tetrahydrofuran or dioxane; an aromatic hydrocarbon such as benzene, toluene, chlorobenzene or xylene; an aprotic polar solvent such as dimethylformamide, ethyl acetate or hexamethylphosphoric triamide; or a mixture of such solvents.

The reaction temperature is usually from −100° C. to the boiling point of the solvent used for the reaction, preferably from −70° C. to 50° C.

The reaction time is usually from 5 minutes to 7 days, preferably from 10 minutes to 24 hours.

Further, it is preferred to carry out the above reaction in the presence of a base. The base may, for example, be sodium hydride, n-butyllithium, sodium methoxide, potassium tert-butoxide, sodium hydroxide or potassium hydroxide.

Such a base is used in an amount of one mol or an excess molar amount, preferably from 1 to 5 mols, per mol of the compound represented by general formula (X).

After completion of the reaction, conventional treatment may be carried out as it is when no protecting group is present in the product, or after removing any protecting group, when such a protecting group is present in the product, to obtain a compound represented by general formula (I-c).

Removal of protecting groups and post-treatment can be carried out by the methods described in the above process 1.

Process 5

A compound represented by general formula (I-d):

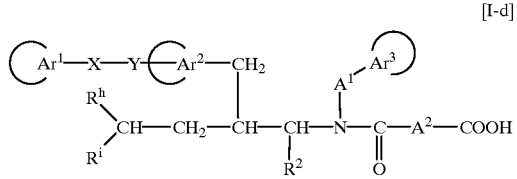

[I-d]

[wherein

$A^1$, $A^2$, $R^2$, $R^h$, $R^i$, X and Y are the same as defined above] can be prepared by reducing a compound represented by general formula (IV-c):

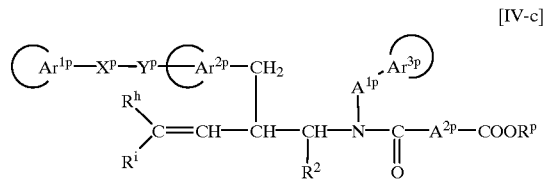

[IV-c]

[wherein

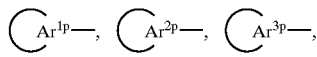

$A^{1p}$, $A^{2p}$, $R^2$, $R^h$, $R^i$, $R^p$, $X^p$ and $Y^p$ are the same as defined above] and, if necessary, removing any protecting group.

Process 5 is a process for producing a compound represented by general formula (I) of the present invention wherein $R^1$ is a group represented by:

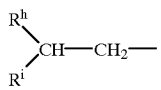

(wherein $R^h$ and $R^i$ are the same as defined above), i.e. a compound represented by general formula (I-d).

The reduction of a compound represented by general formula (IV-c) is usually preferably carried out in an inert solvent and by catalytic reduction using a palladium-carbon catalyst, a Raney nickel catalyst or a platinum catalyst.

Such an inert solvent may, for example, be an alcohol such as methanol, ethanol or propanol or acetic acid.

The reaction temperature is usually from −20° C. to 100° C., preferably from 0° C. to room temperature.

The reaction time is usually from 5 minutes to 7 days, preferably from 10 minutes to 24 hours.

The preferable hydrogen pressure for the catalytic reduction is usually from atmospheric pressure to 5 atm. The catalyst is usually used in an amount of from 0.01 to 1 mol, preferably from 0.05 to 0.2 mol, per mol of the starting compound (IV-c).

After completion of the reaction, conventional treatment may be carried out as it is when no protecting group is present in the product, or after removing any protecting group, when such a protecting group is present in the product, to obtain a compound represented by general formula (I-d).

Removal of protecting groups and post-treatment can be carried out by the methods described in the above process 1.

Process 6

A compound represented by general formula (I-e):

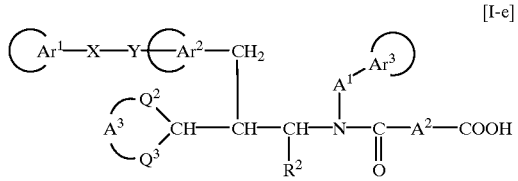

[I-e]

[wherein $A^3$ is a $C_{1-4}$ chain hydrocarbon group which may have substituent(s) selected from the group consisting of a halogen atom, a hydroxyl group, an amino group, a nitro group, a cyano group, a carboxyl group, a lower alkyl group, a lower alkenyl group, a lower alkoxy group, a lower hydroxyalkyl group, a lower fluoroalkyl group, a lower alkoxycarbonyl group, a carbamoyl group and a lower alkylcarbamoyl group; each of $Q^2$ and $Q^3$ which are the same or different, is an oxygen atom or a group represented by —$NR^j$— (wherein $R^j$ is a hydrogen atom or a lower alkyl group); and

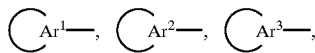

$A^1$, $A^2$, $R^2$, X and Y are the same as defined above] can be prepared by reacting a compound represented by general formula (IX):

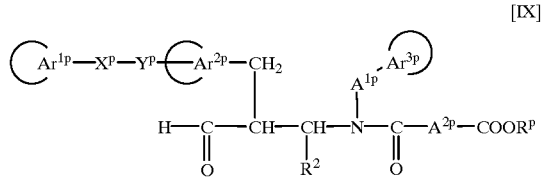

[IX]

[wherein

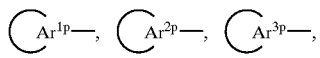

$A^{1p}$, $A^{2p}$, $R^2$, $R^p$, $X^p$ and $Y^p$ are the same as defined above] with a compound represented by general formula (XI):

HQ²—$A^{3p}$—Q³H     (XI)

[wherein $A^{3p}$ is a $C_{1-4}$ chain hydrocarbon group which may have substituent(s) selected from the group consisting of a halogen atom, a nitro group, a cyano group, a lower alkyl group, a lower alkenyl group, a lower alkoxy group, a lower fluoroalkyl group, a lower alkoxycarbonyl group, a carbam-oyl group and a lower alkylcarbamoyl group, and a hydroxyl group, an amino group, a carboxyl group and a lower hydroxyalkyl group which may be protected; and $Q^2$ and $Q^3$ are the same as defined above] to obtain a compound represented by general formula (IV-e):

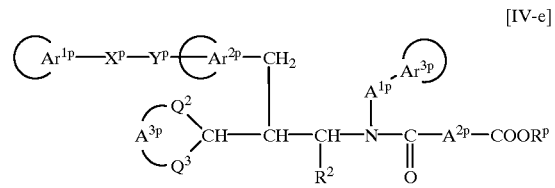

[IV-e]

[wherein

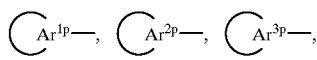

$A^{1p}$, $A^{2p}$, $A^{3p}$, $R^2$, $Q^2$, $Q^3$, $R^p$, $X^p$ and $Y^p$ are the same as defined above] and, if necessary, removing any protecting group.

Process 6 is a process for producing a compound represented by general formula (I) of the present invention wherein $R^1$ is a group represented by:

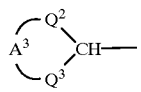

(wherein $A^3$, $Q^2$ and $Q^3$ are the same as defined above), i.e. a compound represented by general formula (I-e).

The reaction of the compound represented by general formula (IX) with the compound represented by general formula (XI) is conducted usually by using 1 mol or an excess molar amount, preferably from 1 to 5 mols, of the compound represented by general formula (XI), per mol of the compound represented by general formula (IX).

The reaction is conducted usually in an inert solvent. The inert solvent may, for example be a halogenated hydrocarbon such as methylene chloride, chloroform, carbon tetrachloride, dichloroethane or trichloroethylene; an ether such as ethyl ether, tetrahydrofuran or dioxane; an aromatic hydrocarbon such as benzene, toluene, chlorobenzene or xylene, or a mixture of such solvents.

The reaction temperature is usually from –70° C. to the boiling point of the solvent used for the reaction, preferably from –20° C. to 120° C.

The reaction time is usually from 5 minutes to 7 days, preferably from 10 minutes to 24 hours.

Further, the above reaction can be carried out in the presence of an acid to facilitate the reaction.

As such an acid, it is preferred to conduct the reaction in the presence of an organic acid such as p-toluenesulfonic acid, methanesulfonic acid or pyridinium p-toluenesulfonate; a Lewis acid such as aluminum chloride, boron trifluoride-ether complex or zinc chloride or an inorganic acid such as hydrochloric acid or sulfuric acid.

Such an acid is used usually in an amount of from 0.001 to 0.1 mol, preferably from 0.001 to 0.01 mol, per mol of the compound represented by general formula (IX).

After completion of the reaction, the product is subjected to usual treatment after removing any protecting group is such a protecting group is present or directly if no such protecting group is present, to obtain a compound represented by general formula (I-e).

Removal of the protecting group and the post treatment may be conducted by the methods described with respect to the above Process 1.

Process 7

A compound represented by general formula (I-f):

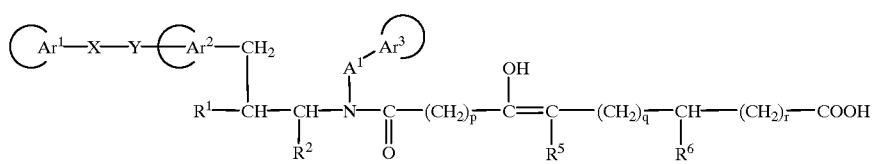

[I-f]

[wherein

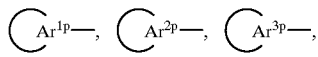

$A^1$, $R^1$, $R^2$, $R^5$, $R^6$, p, q, r, X and Y are the same as defined above] can be prepared by oxidizing a compound represented by general formula (IV-f):

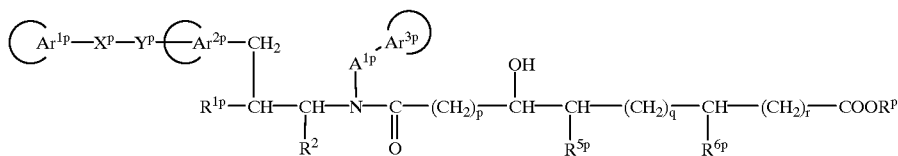

[IV-f]

[wherein $R^{5p}$ is a hydrogen atom, a lower alkoxycarbonyl group or a lower alkenyloxycarbonyl group, or a lower hydroxyalkyl group or a carboxyl group which may be protected, $R^{6p}$ is a hydrogen atom, or a hydroxyl group or a carboxyl group which may be protected; and

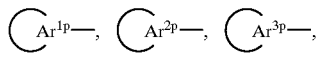

$A^{1p}$, $R^{1p}$, $R^2$, $R^p$, p, q, r, $X^p$ and $Y^p$ are the same as defined above] and, if necessary, removing any protecting group.

Process 7 is a process for producing a compound represented by general formula (I) of the present invention wherein $A^2$ is a group represented by formula (b):

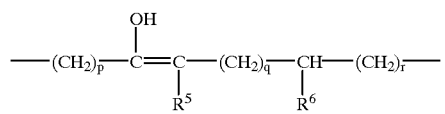

[b]

(wherein $R^5$, $R^6$, p, q and r are the same as defined above), i.e. a compound represented by general formula (I-f).

The reaction of oxidizing the compound represented by general formula (IV-f) is usually preferably carried out in an inert solvent by using so-called Dess-Martin oxidation employing 12-I-5 triacetoxyperiodinane; so-called Swern oxidation employing oxalyl chloride and dimethyl sulfoxide; a sulfur trioxide-pyridine complex; pyridinium chlorochromate; active manganese dioxide; or tetra-n-propylammonium perruthenate.

The inert solvent may, for example, be a halogenated hydrocarbon such as methylene chloride, chloroform or dichloroethane; an ether such as ethyl ether, tetrahydrofuran or dioxane; an aprotic polar solvent such as acetonitrile, acetone, ethyl acetate or dimethyl sulfoxide; or a mixture of such solvents.

The reaction temperature varies depending upon the type of the oxidizing agent, etc. However, it is usually from −100° C. to the boiling point of the solvent used for the reaction, preferably from −70° C. to 100° C.

The reaction time is usually from 5 minutes to 7 days, preferably from 10 minutes to 24 hours.

After completion of the reaction, the product is subjected to usual treatment after removing a protecting group when such a protecting group is present, or directly when no such protecting group is present, to obtain the compound represented by general formula (I-f).

The removal of the protecting group and the post-treatment may be conducted in the same manner as described above with respect to process 1.

Further, a compound corresponding to the compound represented by general formula (IV-f) to be used as the starting material in the above process 7, can be prepared, for example, by hydrolyzing a compound represented by general formula (IV-f-1):

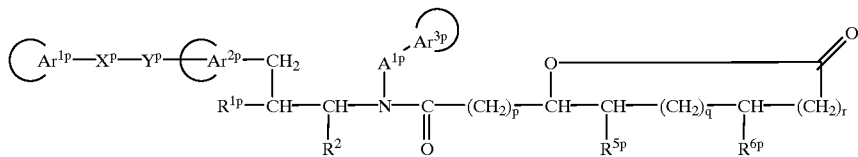
[IV-f-1]

[wherein

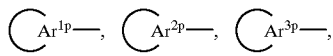

$A^{1p}$, $R^{1p}$, $R^2$, $R^{5p}$, $R^{6p}$, $R^p$, p, q, r, $X^p$ and $Y^p$ are the same as defined above] in the presence of a base, to obtain a compound represented by general formula (IV-f-2):

the methods disclosed in literature (J. Med. Chem., 10, 717 (1967); ibid., 725; Chem. Lett., 191 (1980); ibid., 93 (1982); ibid., 375 (1984); J. Chem. Soc. Chem. Commun., 579 (1984); Tetrahedron Letters, 36, 7459 (1995); Helvetica Chimica Acta, 62, 375 (1984)) or methods similar thereto, or in accordance with the following processes or the methods disclosed in Reference Examples.

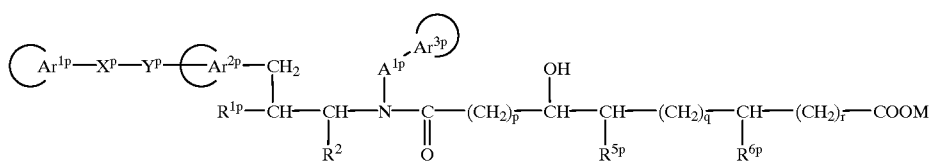
[IV-f-2]

[wherein M is a hydrogen atom or an alkali metal atom;

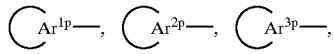

$A^{1p}$, $R^{1p}$, $R^2$, $R^{5p}$, $R^{6p}$, $R^p$, p, q, r, $X^p$ and $Y^p$ are the same as defined above] and then reacting thereto a diazo compound represented by the general formula

(wherein $R^{pp}$ is a lower alkyl group, a lower alkenyl group, an aralkyl group or a lower alkoxycarbonylalkyl group), or an alkylating agent represented by the general formula $R^{pp}$—Z (wherein $R^{pp}$ and Z are the same as defined above).

Isolation and purification of the compound represented by general formula (I), (I-a), (I-b), (I-c), (I-d), (I-e) or (I-f) obtained by the above process can be conducted by a single use or a proper combination of conventional separating means such as column chromatography employing silica gel, adsorbent resin, etc., liquid chromatography, solvent extraction and recrystallization-reprecipitation.

The compound represented by general formula (I), (I-a), (I-b), (I-c), (I-d), (I-e) or (I-f) can be converted to a pharmaceutically acceptable sale or ester by a conventional method. Reversely, the conversion from the salt or ester to a free carboxylic acid can also be conducted by a conventional method.

The compounds represented by general formulas (II), (III), (V), (VI), (VII), (VIII), (IX), (X), (XI) may be commercially available or can be prepared in accordance with Process A

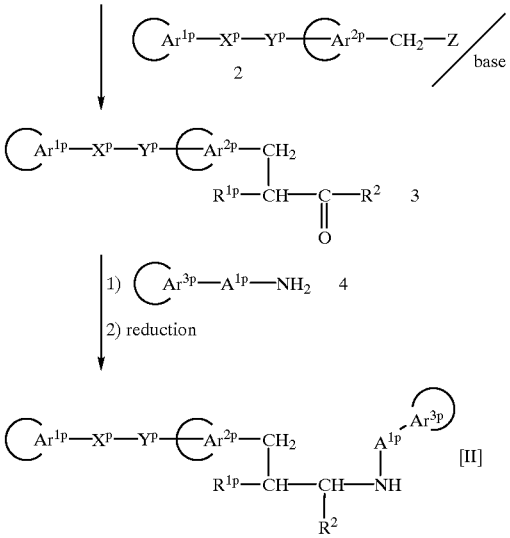

[wherein

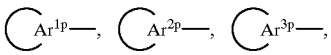

$A^{1p}$, $R^{1p}$, $R^2$, $X^p$ $Y^p$ and Z are the same as defined above]

By this process, the desired compound (II) can be prepared by reacting a ketone compound 1 represented by general formula 1 with an alkylating agent represented by general formula 2 to produce a compound represented by general formula 3, then reacting the compound 3 with an amine compound represented by general formula 4, followed by reduction.

The above reaction steps will be described in detail referring to suitable reaction conditions, etc.

The first step of preparing the compound represented by general formula 3 from the ketone compound 1, can be conducted by reacting an equimolar amount or an excess molar amount, preferably from 1 to 2 mols, of the alkylating agent represented by general formula 2 to the ketone compound 1 in the presence of a base in an inert solvent which does not adversely affect the reaction or without using any solvent.

The inert solvent may, for example, be an ether such as ethyl ether, tetrahydrofuran or dioxane; an aromatic hydrocarbon such as benzene, toluene or xylene; an aprotic polar solvent such as dimethylformamide, dimethyl sulfoxide or hexamethylphosphoric triamide, or a mixture of such solvents.

The base to be used for this reaction, may, for example, be an alkali metal hydride such as sodium hydride, lithium hydride or potassium hydride; a lithium amide such as lithium amide, lithium diisopropylamide or lithium bis(trimethylsilyl)amide; an alkyllithium such as methyllithium, butyllithium or tert-butyllithium; an alkali metal alkoxide such as sodium methoxide, sodium ethoxide or potassium tert-butoxide; or an alkali metal hydroxide such as sodium hydroxide, potassium hydroxide or lithium hydroxide.

The base is used usually in an amount of 1 mol or an excess molar amount, preferably from 1 to 5 mols, per mol of the starting material alkylating agent 2.

The reaction temperature is usually from −100° C. to the boiling point of the solvent used for the reaction, preferably from −80° C. to 100° C. The reaction time is usually from 10 minutes to 48 hours, preferably from 30 minutes to 24 hours.

The step of preparing the desired compound (II) from the compound represented by general formula 3 can be conducted usually in an inert solvent such as methanol, ethanol, benzene, ethyl ether or tetrahydrofuran by reacting 1 mol or an excess molar amount, preferably from 1 to 2 mols, of the amine compound represented by general formula 4 with 1 mol of the compound represented by general formula 3 to preliminarily form an imine, which is subsequently reduced.

The reaction temperature in the process for forming the above imine is usually from 0° C. to the boiling point of the solvent used for the reaction, preferably from room temperature to 100° C. The reaction time is usually from 5 minutes to 48 hours, preferably from 30 minutes to 24 hours. After the formation of the imine, the reaction solution may be used as it is to the subsequent step of the reduction reaction, or the reaction solution may be distilled or subjected to a conventional separation means to isolate the imine compound, with is then subjected to the subsequent reduction.

The reduction can be carried out by using a metal hydride complex such as sodium borohydride, sodium cyanoborohydride or lithium aluminum hydride, or by catalytic reduction employing a palladium-carbon catalyst or a Raney nickel catalyst When a metal hydride complex is used as a reducing agent, the reducing agent is used usually in an amount of 1 mol or an excess molar amount, preferably from 1 to 5 mols, per mol of the above imine.

For the reduction, an inert solvent, for example, an alcohol such as methanol or ethanol; an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene or toluene; or a mixture of such solvents, can be used appropriately as a solvent depending upon the type of the reducing agent.

The reaction temperature is usually from 0° C. to room temperature, and the reaction time is usually from 1 hour to 6 hours.

The compounds represented by general formula 1, 2 and 4 may be commercially available or can be produced by a proper combination, as the case requires, of the methods disclosed in Reference Examples, or conventional methods or methods similar thereto.

Process B

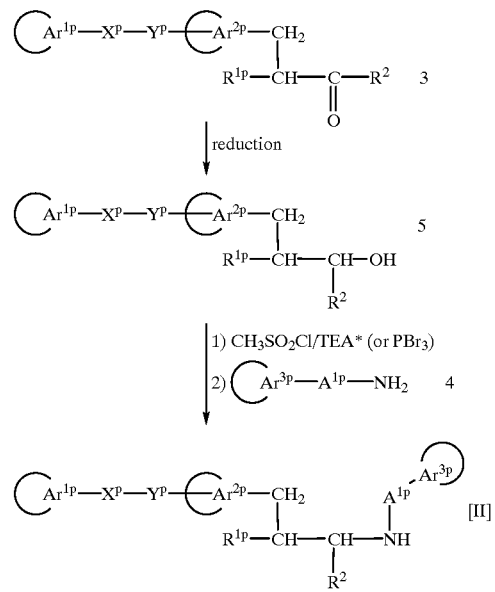

*triethylamine

[wherein

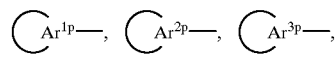

$A^{1p}$, $R^{1p}$, $R^2$, $X^p$ and $Y^p$ are the same as defined above].

According to this process, the desired compound (II) can be prepared by reacting a reducing agent such as a metal hydride complex to a compound represented by general formula 3 to obtain an alcohol compound 5 and reacting an amine compound represented by general formula 4 to the alcohol compound 5.

The above reaction steps will be described in detail referring to suitable reaction conditions, etc.

The step of reducing the compound represented by general formula 3 to the alcohol compound 5 can be conducted usually by using a metal hydride complex such as sodium borohydride, diisobutylaluminum hydride, lithium aluminum hydride or lithium tri-sec-butylborohydride (L-selectride™), or by catalytic reduction employing e.g. a palladium-carbon catalyst or a Raney nickel catalyst, in an inert solvent which does not adversely affect the reaction.

When the metal hydride complex is used as the reducing agent, such a reducing agent is used usually in an amount of 1 mol or an excess molar amount, preferably from 1 to 5 mols, per mol of the compound represented by general formula 3.

The inert solvent to be used in this reaction may be suitably selected depending upon the type of the reducing agent.

For example, when the reducing agent is sodium borohydride, an inert solvent, such as an alcohol such as methanol or ethanol; an ether such as dimethoxyethane, dioxane, tetrahydrofuran or diglyme; an aprotic polar solvent such as dimethylformamide or dimethylacetamide, or water, or a solvent mixture thereof, may be used, and particularly preferred is an alcohol such as methanol or ethanol.

For example, when the reducing agent is diisobutylaluminum hydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; an aromatic hydrocarbon such as benzene or toluene; or methylene chloride, or a solvent mixture thereof, may be used, and particularly preferred is toluene or methylene chloride;

For example, when the reducing agent is lithium aluminum hydride or lithium tri-sec-butylborohydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene or toluene, or a solvent mixture thereof, may be used, and particularly preferred is ethyl ether or tetrahydrofuran.

For the catalytic reduction, the solvent is preferably an alcohol such as methanol or ethanol.

The reaction temperature and the reaction time vary depending upon the stability and the susceptibility to the reduction reaction of the starting material ketone compound 3, the type of the reducing agent and the type of the solvent. However, the reaction temperature is usually from –80° C. to 100° C., preferably from –70° C. to 40° C., and the reaction time is usually from 5 minutes to 2 days, preferably from 30 minutes to 24 hours.

The step of preparing the desired compound (II) from a compound represented by general formula 5 can be carried out by reacting a sulfonating agent such as methanesulfonyl chloride to the alcohol compound represented by general formula 5 in the presence of a base, or reacting a halogenating agent such as thionyl chloride or phosphorus tribromide therewith, to convert the hydroxyl group in the formula to a leaving group, followed by reacting an amine compound represented by general formula 4.

The reaction for introducing the leaving group can be conducted usually by reacting 1 mol or an excess molar amount, preferably from 1 to 2 mols, of a sulfonating agent and a base such as triethylamine to 1 mol of the alcohol compound 5 in an inert solvent such as methylene chloride, chloroform, benzene, tetrahydrofuran or ethyl acetate, or using 1 mol or an excess molar amount, preferably from 1 to 5 mols, of a halogenating agent.

The reaction temperature is usually from –70° C. to the boiling point of the solvent used for the reaction, preferably from –20° C. to 80° C., and the reaction time is usually from 5 minutes to 48 hours, preferably from 30 minutes to 24 hours.

Then, the step of reacting an amine compound 4 to the compound having the leaving group introduced, obtained by the above reaction, can be conducted usually by employing 1 mol or an excess molar amount, preferably from 1 to 50 mols, of the amine compound 4 per mol of the starting compound having the leaving group, in an inert solvent such as methylene chloride, chloroform, benzene, ethyl ether or tetrahydrofuran.

If necessary, this reaction can be conducted in the presence of a base other than the amine compound represented by general formula 4.

As such a base, an inorganic base such as sodium hydroxide, potassium hydroxide, calcium hydroxide, sodium carbonate, potassium carbonate or sodium hydrogencarbonate, or an organic base such as triethylamine, N-ethyldiisopropylamine, pyridine or N,N-dimethylaniline may, for example, be mentioned.

Such a base is used usually in an amount of 1 mol or an excess molar amount, preferably from 1 to 5 mols, per mol of the starting material compound.

The reaction temperature is usually from –50° C. to 150° C., preferably from –20° C. to 100° C., and the reaction time is usually from 5 minutes to 7 days, preferably from 10 minutes to 24 hours.

Process C

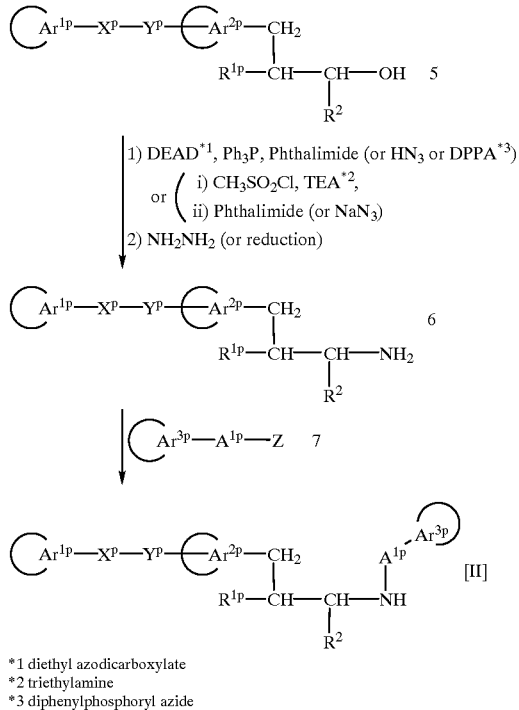

*1 diethyl azodicarboxylate
*2 triethylamine
*3 diphenylphosphoryl azide

[wherein

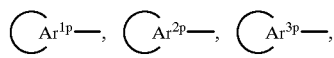

$A^{1p}$, $R^{1p}$, $R^2$, $X^p$, $Y^p$ and Z are the same as defined above].

According to this process, the desired compound (II) can be prepared by reacting diethyl azodicarboxylate, triphenylphosphine and phthalimide (or hydrogen azide or diphenylphosphoryl azide) or reacting a sulfonylating agent such as methanesulfonyl chloride in the presence of a base such as triethylamine, then reacting phthalimide (or sodium azide) in the presence of a base, to the alcohol compound represented by general formula 5, to obtain a phthalimide-protected form (or an azide compound) of the amine compound 6, then reacting hydrazine (or a reducing agent) to remove the phthalimido group (or reduce the azido group) to obtain an amine compound represented by general formula 6, and finally reacting a compound represented by general formula 7 to the compound 6.

The above reaction steps will be described in detail referring to suitable reaction conditions, etc.

For the step of producing the compound represented by general formula 6 from the alcohol compound 5, various synthetic methods and reaction conditions well known in organic synthetic chemistry for converting alcohol compounds to amines, may be employed. For example, it is preferred to employ the so-called Mitsunobu reaction using diethyl azodicarboxylate, triphenylphosphine and phthalimide (or hydrogen azide or diphenylphosphoryl azide) or a method which comprises sulfonylation with a sulfonfylating agent such as methanesulfonyl chloride in the presence of a base such as triethylamine, then reacting phthalimide (or sodium azide) in the presence of a base, and then treating (or reducing) the obtained phthalimide (or azide) compound with hydrazine.

The above reactions are conducted usually in a solvent inert to the reaction. The inert solvent may, for example, preferably be tetrahydrofuran, dimethoxyethane, benzene or toluene in the case of the above-mentioned Mitsunobu reaction; methylene chloride, chloroform, tetrahydrofuran, benzene, ethyl acetate or dimethylformamide in the case of the sulfonylation followed by the reaction with phthalimide (or sodium azide); an alcohol such as methanol or ethanol in the next step of the phthalimide-removing reaction with hydrazine; an ether such as ethyl ether or tetrahydrofuran in the case where a metal hydride complex is used as the reducing agent in the reduction reaction of the azide compound; hydrous tetrahydrofuran in the case where phosphine reduction is conducted with triphenylphosphine or the like; and an alcohol such as methanol or ethanol in the reduction by catalytic reduction.

With respect to the amount of the reagents to be used, in the above Mitsunobu reaction, each of diethyl azodicarboxylate, triphenylphosphine and phthalimide (or hydrogen azide or diphenylphosphoryl azide) is used in an amount of 1 mol or an excess molar amount, preferably from 1 to 5 mols, per mol of the starting material alcohol compound 5. In the reaction with the phthalimide (or sodium azide) after the sulfonylation, the sulfonylating agent such as methanesulfonyl chloride is used in an amount of 1 mol or an excess molar amount, preferably from 1 to 2 mols, per mol of the alcohol compound 5, and the base such as triethylamine used at that time is usually in an amount of 1 mol or an excess molar amount, preferably from 1 to 2 mols, per mol of the sulfonylating agent. In the next step of the reaction with phthalimide (or sodium azide) in the presence of a base, 1 mol or an excess molar amount, preferably from 1 to 5 mols of each of phthalimide and the base (or sodium azide) is used per mol of the sulfonylating agent. Here, the base to be used together with phthalimide is preferably sodium carbonate or potassium carbonate. Otherwise, without using such a base, a sodium salt or a potassium salt of phthalimide may be used by itself. Then, in the reaction for removing the phthalimido group with hydrazine, hydrazine is used in an amount of 1 mol or an excess molar amount, preferably from 1 to 10 mols, per mol of the phthalimide compound as the starting material compound. In the reduction of the azide compound with a metal hydride complex or with triphenylphosphine, the reducing agent is used usually in the amount of 1 mol or an excess molar amount, preferably from 1 to 2 mols, per mol of the azide compound.

In the case of the above Mitsunobu reaction, the reaction temperature is usually from −70° C. to 100° C., preferably from −20° C. to 50° C., and the reaction time is usually from 5 minutes to 48 hours, preferably from 30 minutes to 24 hours. In the reaction for removing the phthalimido group by hydrazine, the reaction temperature is usually from 0° C. to the boiling point of the solvent used for the reaction, preferably from room temperature to 100° C., and the reaction time is usually from 5 minutes to 48 hours, preferably from 30 minutes to 24 hours. In the reaction for converting the azide compound to the amine compound by reduction, when a metal hydride complex is used as the reducing agent, the reaction temperature is usually from −70° C. to 150° C., preferably from −20° C. to 50° C., and the reaction time is usually from 5 minutes to 48 hours, preferably from 10 minutes to 10 hours. When triphenylphosphine is used as the reducing agent, the reaction temperature is usually from room temperature to the boiling point of the solvent used for the reaction, preferably from 30° C. to 100° C., and the reaction time is usually from 10 minutes to 48 hours, preferably from 30 minutes to 24 hours. Further, in the case of the reduction by catalytic reduction, the reaction temperature is usually from 0° C. to 100° C., preferably from room temperature to 50° C., and the reaction time is usually from 10 minutes to 48 hours, preferably from 10 minutes to 24 hours.

The step of producing the desired compound (II) from the compound represented by general formula 6 is carried out usually in a solvent inert to the reaction and can be carried out by reacting 1 mol or an excess molar amount, preferably from 1 to 2 mols, of the alkylating agent represented by general formula 7 to 1 mol of the amine compound 6 in the presence of a base.

Such an inert solvent may, for example, be an ether such as ethyl ether, tetrahydrofuran or dioxane; an aromatic hydrocarbon such as benzene, toulene or xylene; an aprotic polar solvent such as dimethylformamide, dimethyl sulfoxide or hexamethylphosphoric triamide, or a mixture of such solvents.

The base to be used in this reaction, may, for example, be an alkali metal hydride such as sodium hydride, lithium hydride or potassium hydride; a lithium amide such as lithium amide, lithium diisopropylamide or lithium bistrimethylsilylamide; an alkyllithium such as methyllithium, butyllithium or tert-butyllithium; an alkali metal alkoxide such as sodium methoxide, sodium ethoxide or potassium tert-butoxide; an alkali metal hydroxide such as sodium hydroxide, potassium hydroxide or lithium hydroxide; or an alkali metal carbonate such as sodium carbonate or potassium carbonate.

Such a base is used usually in an amount of 1 mol or an excess molar amount, preferably from 1 to 5 mols, per mol of the starting material alkylating agent 7.

The reaction temperature is usually from −100° C. to the boiling point of the solvent used for the reaction, preferably from −80° C. to 100° C., and the reaction time is usually from 10 minutes to 48 hours, preferably from 30 minutes to 24 hours.

Further, the compound represented by general formula 7 may be commercially available or can be produced by a proper combination, as the case requires, of the methods disclosed in Reference Examples, or conventional methods or methods similar thereto.

Process D

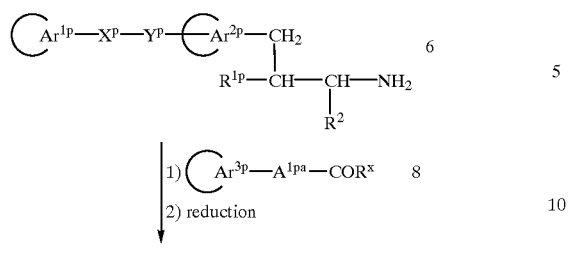

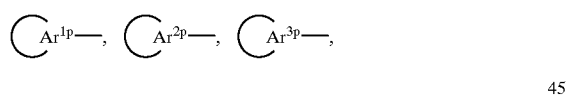

[wherein $A^{1pa}$ is a $C_{1-5}$ chain hydrocarbon group which may have substituent(s) selected from the group consisting of a halogen atom, a lower alkyl group, an oxo group, a lower hydroxyalkyl group which may be protected and a lower alkoxy group or a group represented by $-A^{1cp}-W^{1p}-A^{1bp}-$ (wherein $A^{1cp}$ is a $C_{1-4}$ chain hydrocarbon group which may have substituent(s) selected from the group consisting of a halogen atom, a lower alkyl group, an oxo group, a lower hydroxyalkyl group which may be protected and a lower alkoxy group; $A^{1bp}$ is a single bond or a $C_{1-4}$ chain hydrocarbon group which may have substituent(s) selected from the group consisting of a halogen atom, a lower alkyl group, an oxo group, a lower hydroxyalkyl group which may be protected and a lower alkoxy group; $W^{1p}$ is an oxygen atom, a sulfur atom, an ethynylene group, a cyclopropylene group or a group represented by $-NR^{wp}-$; and $R^{wp}$ is a hydrogen atom, a lower alkyl group or a protecting group for an imino group); $R^x$ is a hydrogen atom or a lower alkyl group; and $A^{1p}$, $R^{1p}$, $R^2$, $X^p$ and $Y^p$ are the same as defined above]

According to this process, the desired compound (II-a) can usually be prepared by preliminarily forming an imine by reacting 1 mol or an excess molar amount, preferably from 1 to 2 mols of the compound represented by general formula 8 to 1 mol of the amine compound represented by general formula 6 in an inert solvent such as methanol, ethanol, benzene, ethyl ether or tetrahydrofuran, and then reducing it.

This reaction can be carried out in the same manner as the step for producing the desired compound (II) from the compound represented by general formula 3 in the above process A. Accordingly, with respect to the reaction conditions, etc., similar conditions may be employed.

Further, the compound represented by general formula 8 may be commercially available or can be produced by a proper combination, as the case requires, of the methods disclosed in Reference Examples, or conventional methods or methods similar thereto.

Process E

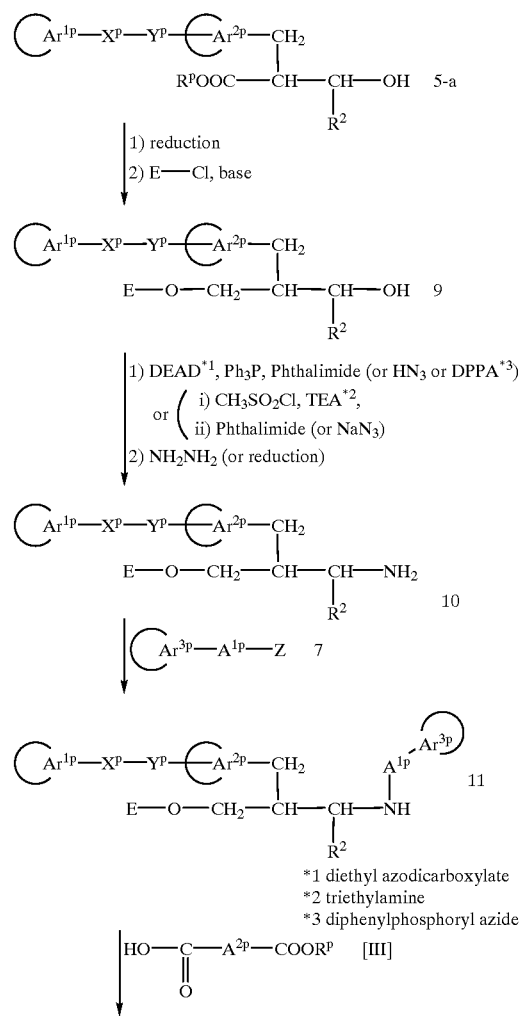

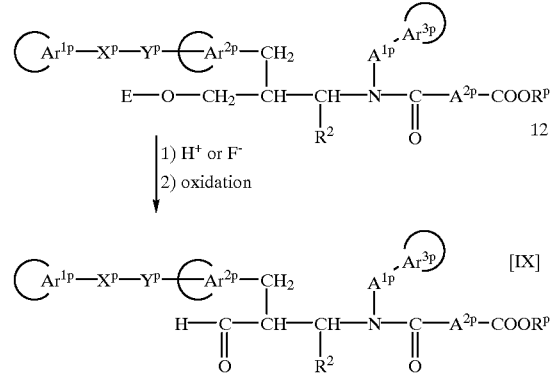

[wherein E is a trityl group or a tert-butyldimethylsily group; and

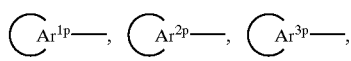

$A^{1p}$, $A^{2p}$, $R^2$, $R^p$, $X^p$, $Y^p$ and Z are the same as defined above]

According to this process, the desired compound (IX) can be prepared by reducing a compound represented by general formula 5-a to a diol compound, selectively protecting only the primary hydroxyl group of the diol compound to obtain a compound represented by general formula 9, and then reacting the compound 9 with diethyl azodicarboxylate, triphenylphosphine and phthalimide (or hydrogen azide or diphenylphosphoryl azide) or reacting the compound 9 with a sulfonylating agent such as methanesulfonyl chloride in the presence of a base such as triethylamine, and then reacting phthalimide (or sodium azide) in the presence of a base, to obtain a phthalimide-protected form (or an azide compound) of the amine compound 10, then reacting hydrazine (or a reducing agent) to remove the phthalimido group (or reduce the azide group) to obtain an amine compound represented by general formula 10, reacting a compound represented by general formula 7 to the compound 10 to obtain a compound represented by general formula 11, reacting a carboxylic acid represented by general formula (III) or its reactive derivative to the compound to obtain a compound represented by general formula 12, then removing the protecting group for the primary hydroxyl group of the compound 12 and then oxidizing the compound 12.

The above reaction steps will be described in detail referring to suitable reaction conditions, etc.

The step of reducing the compound represented by general formula 5-a to the diol compound 9 can be conducted usually by using a metal hydride complex such as sodium borohydride, lithium borohydride, diisobutylaluminum hydride, lithium aluminum hydride or lithium tri-sec-butylborohydride (L-selectride™) in an inert solvent which does not adversely affect the reaction.

The reducing agent is used usually in an amount of 1 mol or an excess molar amount, preferably from 1 to 5 mols, per mol of the compound represented by general formula 5-a.

The inert solvent to be used in this reaction may be suitably selected depending upon the type of the reducing agent.

For example, when the reducing agent is sodium borohydride or lithium borohydride, an inert solvent, such as an alcohol such as methanol or ethanol; an ether such as dimethoxyethane, dioxane, tetrahydrofuran or diglyme; an aprotic polar solvent such as dimethylformamide or dimethylacetamide, or water, or a solvent mixture thereof, may be used, and particularly preferred is an alcohol such as methanol or ethanol.

For example, when the reducing agent is diisobutylaluminum hydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cylcohexane; an aromatic hydrocarbon such as benzene or toluene; methylene chloride, or a solvent mixture thereof, may be used, and particularly preferred is toluene or methylene chloride.

For example, when the reducing agent is lithium aluminum hydride or lithium tri-sec-butylborohydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene or toluene, or a solvent mixture thereof, may be used, and particularly preferred is ethyl ether or tetrahydrofuran.

The reaction temperature and the reaction time vary depending upon the stability ad the susceptibility to the reduction reaction of the starting material compound 5-a, the type of the reducing agent and the type of the solvent. However, the reaction temperature is usually from −80° C. to 100° C., preferably from −70° C. to 40° C., and the reaction time is usually from 5 minutes to 2 days, preferably from 30 minutes to 24 hours.

The next step of producing the compound 9 by selectively protecting the primary hydroxyl group of the diol compound obtained by the reduction can be carried out by using a trityl group or a tert-butyldimethylsilyl group as a protecting group and by reacting 1 mol or an excess molar amount, preferably from 1 to 1.5 mols of trityl chloride or tert-butyldimethylchlorosilane, per mol of the diol compound in an inert solvent which does not adversely affect the reaction in the presence of a base.

The inert solvent may, for example, be methylene chloride, tetrahydrofuran or dimethylformamide, and the base may, for example, be triethylamine, 4-dimethylaminopyridine or imidaxole.

The reaction temperature is usually from −20° C. to the boiling point of the solvent used for the reaction, preferably from 0° C. to room temperature, and the reaction time is usually from 10 minutes to 7 days, preferably from 30 minutes to 24 hours.

Each of the steps of producing the compound represented by general formula 11 from the compound represented by general formula 9 can be carried out in the same manner as in each of the steps of producing the compound represented by general formula (II) from the alcohol compound represented by general formula 5 in the above process C. Accordingly, with respect to each of the reaction conditions, etc., similar conditions may be employed respectively.

The step of producing a compound represented by general formula 12 from the compound represented by general formula 11, can be carried out in the same manner as in the reaction of the compound represented by general formula (II) with the carboxylic acid represented by general formula (III) or its reactive derivative in the above Process 1. Accordingly, with respect to the reaction conditions, etc., similar conditions may be employed.

The step of removing the protecting group for the primary hydroxyl group represented as E from the compound represented by general formula 12 can be usually carried out in a solvent inert to the reaction depending on the kind of the protecting group, from example, by treating with an acid such as acetic acid, formic acid, trifluoroacetic acid, hydrochloric acid, sulfuric acid or p-toluenesulfonic acid when the protecting group is a trityl group, or with a similar acid or a fluoride salt such as tetrabutylammonium fluoride or potassium fluoride when the protecting group is a tert-butyldimethylsilyl group.

The reaction solvent varies depending on the kind of the reaction and the stability of the compound. However, as the solvent, for example, methylene chloride, methanol, ethanol, tetrahydrofuran or a solvent mixture of such a solvent and water is preferred in the case of treatment with an acid, and especially, when acetic acid, formic acid or trifluoroacetic acid is used as the acid, it is preferred to conduct the reaction by using the acid itself or a mixture of the acid and water as the solvent. Further, when a fluoride salt such as tributylammonium fluoride or potassium fluoride is used, for example, tetrahydrofuran, methylene chloride or dimethylformamide is preferred.

The reaction temperature is usually from −20° C. to the boiling point of the solvent to be used for the reaction, preferably from −20° C. to 50° C., and the reaction time is usually from 10 minutes to 48 hours, preferably from 30 minutes to 24 hours, in both case of treatment with an acid and use of a fluoride salt.

The step of oxidizing the primary alcohol compound obtained by the above reaction to the desired compound (IX)

is usually carried out in an solvent inert to the reaction by using, for example, pyridinium chlorochromate, pyridinium dichromate, a sulfur trioxidepyridine complex, oxalyl chloride and dimethyl sulfoxide (under conditions for the so-called Swern oxidation) or 12-I-5 triacetoxyperiodinane (Dess-Martin reagent) as an oxidizing agent.

As the inert solvent, for example, a halogenated hydrocarbon such as methylene chloride or chloroform is usually preferred. The amount of an oxidizing agent is usually 1 mol or an excess molar amount, preferably from 1 to 2 mols, per mol of the starting material alcohol.

The reaction temperature is usually from −80° C. to the boiling point of the solvent used for the reaction, preferably from −80° C. to 0° C. when oxalyl chloride and dimethyl sulfoxide are used as the oxidizing agent, and from −20° C. to room temperature when other oxidizing agent is used.

The reaction time is usually from 10 minutes to 48 hours, preferably from 30 minutes to 24 hours irrespective of the kind of the oxidizing agent.

The compound represented by general formula 5-a is a compound represented by general formula 5 wherein $R^{1p}$ is $R^pOOC—$, and therefore can be prepared by the previously mentioned process.

Process F

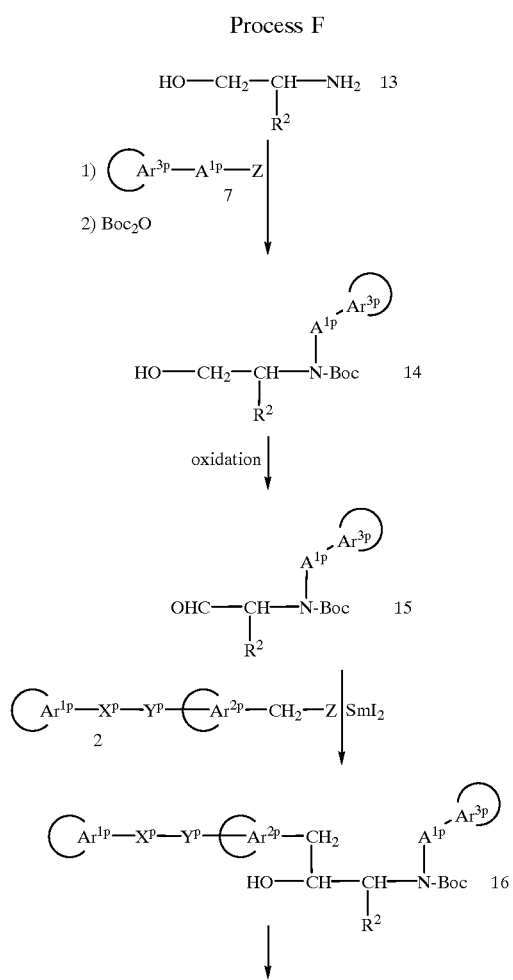

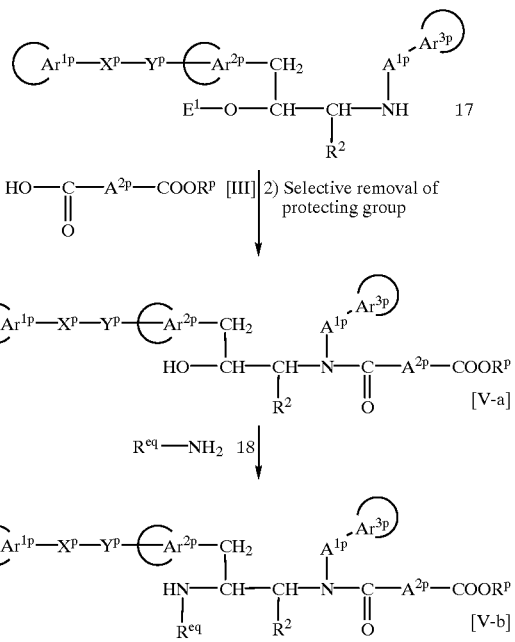

[wherein Boc is a tert-butoxycarbonyl group; $E^1$ is a protecting group for a hydroxyl group; and

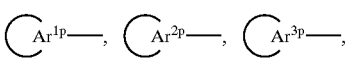

$A^{1p}$, $A^{2p}$, $R^2$, $R^{eq}$, $R^p$, $X^p$, $Y^p$ and Z are the same as defined above]

According to this process, a desired compound (V-a) can be prepared by reacting a compound represented by general formula 13 with a compound represented by general formula 7, protecting the amino group with a tert-butoxycarbonyl group to obtain a compound represented by general formula 14, oxidizing the compound 14 to an aldehyde compound 15, condensing the aldehyde compound 15 with a compound represented by general formula 2 in the presence of samarium iodide to obtain a compound represented by general formula 16, protecting the hydroxyl group of the compound, removing the tert-butoxycarbonyl group to obtain a compound represented by general formula 17, reacting the compound with a carboxylic acid represented by general formula (III) or its reactive derivative, and selectively removing the protecting group represented as $E^1$.

Another desired compound (V-b) can be prepared by converting the hydroxyl group of the compound (V-a) obtained by the above-mentioned process into a leaving group and reacting an amine represented by general formula 18.

The above reaction steps will be described in detail referring to suitable reaction conditions, etc.

The step of reacting a compound represented by general formula 13 with a compound represented by general formula 7 can be carried out in the same manner as the step of producing a compound represented by general formula (II) from an amine compound represented by general formula 6 in the above process C. Accordingly, with respect to the reaction conditions, etc., similar conditions may be employed.

The step of protecting the amino group of the compound obtained by the above reaction can be conducted by methods well known in synthetic organic chemistry, for example, by the known methods disclosed in the literature mentioned for process 1.

The step of oxidizing a compound represented by general formula 14 to an aldehyde 15 is usually preferably carried out in an inert solvent by using the so-called Dess-Martin oxidation employing 12-I-5 triacetoxyperiodinane; the so-called Swern oxidation employing oxalyl chloride and dimethyl sulfoxide; a sulfur trioxide-pyridine complex; pyridinium chlorochromate; active manganese dioxide; or tetra-n-propylammonium perruthenate.

The inert solvent may, for example, be a halogenated hydrocarbon such as methylene chloride, chloroform or dichloroethane; an ether such as ethyl ether, tetrahydrofuran or dioxane; an aprotic polar solvent such as acetonitrile, acetone, ethyl acetate or dimethyl sulfoxide; or a mixture of such solvents.

The reaction temperature varies depending upon the type of the oxidizing agent, etc. However, it is usually from −100° C. to the boiling point of the solvent used for the reaction, preferably from −70° C. to 100° C.

The reaction time is usually from 5 to 7 days, preferably from 10 minutes to 24 hours.

The step of producing a compound represented by general formula 16 by condensing an aldehyde represented by general formula 15 with a compound represented by general formula 2 in the presence of samarium iodide is carried out usually by employing equimolar amounts of the two reactants or using a slightly excess amount of one of them in the presence of an equimolar or slightly excess amount of samarium iodide, in an inert solvent.

Such an inert solvent may, for example, be an ether such as ethyl ether, tetrahydrofuran or dioxane; an aromatic hydrocarbon such as benzene, toulene, chlorobenzene or xylene; and aprotic polar solvent such as dimethylformamide or acetonitrile or a mixture of such solvents.

The reaction temperature is usually from −100° C. to the boiling point of the solvent used for the reaction, preferably from −70° C. to 50° C.

The reaction time is usually from 5 minutes to 7 days, preferably from 10 minutes to 24 hours.

The step of producing a compound represented by general formula 17 by protecting the hydroxyl group of a compound represented by general formula 16 and removing the tert-butoxycarbonyl group can be carried out by methods well known in synthetic organic chemistry, for example, by known methods disclosed in the literature mentioned for the above process 1.

The hydroxyl-protecting group may be the protecting group mentioned above with respect to process 1.

In the step of producing the desired compound (V-a) from the compound represented by general formula 17, the reaction of the compound represented by general formula 17 with the carboxylic acid represented by general formula (III) or its reactive derivative, can be carried out in the same manner as the reaction of the compound represented by general formula (II) with the carboxylic acid represented by general formula (III) or its reactive derivative in the above process 1. Accordingly, with respect to the reaction conditions, etc., similar conditions may be employed.

For the step of selectively removing the protecting group represented as $E^1$ from the compound obtained by the above reaction, various methods may suitably be selected depending upon the type and the characteristics of the protecting group. Namely, utilizing the difference in the stability against an acid, a base or reduction between $E^1$ and other protecting groups, the protecting group can selectively be removed by a conventional means such as an acid, a base or reduction. With respect to specific conditions for such a reaction, the methods disclosed in the known literature mentioned above for process 1.

The step of producing another desired compound (V-b) by converting the hydroxyl group of the compound (V-a) obtained by the above-mentioned process into a leaving group and then reacting an amine represented by general formula 18 can be carried out in the same manner as the step of producing a compound represented by general formula (II) from an amine compound represented by general formula 5 in the above process B. Accordingly, with respect to the reaction conditions, etc., similar conditions may be employed.

Further, the compound represented by general formula 13 may be commercially available, or may be produced by a proper combination, as the case requires, of the methods disclosed in Reference Examples, or conventional methods or methods similar thereto.

Process G

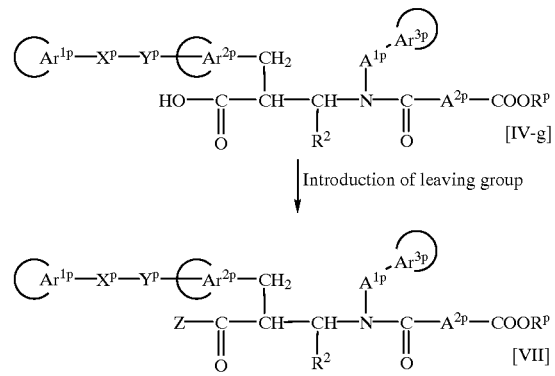

[wherein

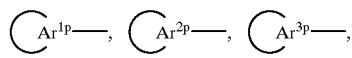

$A^{1p}$, $A^{2p}$, $R^2$, $R^p$, $X^p$, $Y^p$ and Z are the same as defined above]

According to this process, the desired compound (VII) can be prepared by introducing a leaving group to a compound represented by general formula (IV-g).

The reaction can be carried out in the same manner as in the method of introducing a leaving group to the compound represented by general formula 5 in the above process B by using, for example, a halogenating agent such as thionyl chloride, phosphorus trichloride, phosphorus pentachloride, phosphorus oxychloride, phosphorus tribromide, oxalyl chloride or phosgene, or a sulfonating agent such as methanesulfonyl chloride, p-toluenesulfonyl chloride or benzenesulfonyl chloride. Accordingly, with respect to the reaction conditions, etc., similar conditions may be employed.

Process H

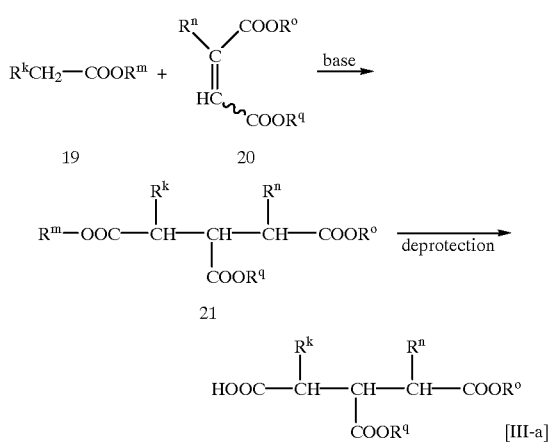

[wherein each of $R^k$ and $R^n$ which are the same or different, is a hydrogen atom, a lower alkyl group, an aryl group or an aralkyl group, each of $R^o$ and $R^q$ which are the same or different, is a carboxyl-protecting group; and $R^m$ is a tert-butyl group, a benzyl group, a benzhydryl group or a trityl group]

Process H is a process for preparing a carboxylic acid derivative represented by general formula (III-a) among the above-mentioned compounds represented by general formula (III).

According to this process, the desired carboxylic acid derivative (III-a) can be prepared by conducting a so-called Michael addition reaction which comprises reacting a maleic acid derivative or a fumaric acid derivative represented by general formula 20 to an ester derivative having a readily removable carboxyl-protecting group $R^m$, represented by general formula 19, in the presence of a base, and then removing the carboxyl-protecting group $R^m$ from the obtained Michael addition product 21 under a mild condition.

As the carboxyl-protecting groups represented as $R^o$ and $R^q$, a lower alkyl group such as a tert-butyl group, or a benzhydryl group, is preferred.

The protecting group $R^m$ is preferably a protecting group which can readily be removed under a mild condition of catalytic reduction or weakly acidic condition and which is stable under the Michael addition reaction condition, such as a tert-butyl group, a benzyl group, a benzhydryl group or a trityl group.

The above Michael addition reaction can be conducted by reacting the compound represented by general formula 20 in an amount of 1 mol or an excess molar amount, preferably from 1 to 2 mols, to 1 mol of the compound represented by general formula 19 in the presence of a base such as sodium hydride, butyllithium, lithium diisopropylamide or lithium bis(trimethylsilyl)amide usually in an inert solvent such as benzene, ethyl ether or tetrahydrofuran.

Such a base is used usually in an amount of 1 mol or a slightly excess molar amount, preferably from 1 to 1.5 mols, per mol of the compound represented by general formula 20.

The reaction temperature is usually from $-100°$ C. to $100°$ C., preferably from $-80°$ C. to room temperature, and the reaction time is usually from 5 minutes to 24 hours, preferably from 10 minutes to 10 hours.

The reaction conditions for the reaction for removing the protecting group from the compound represented by general formula 21 to form the desired carboxylic acid derivative (III-a), vary depending upon the type of the protecting group, etc. For example, when the protecting group is a tert-butyl group, a benzhydryl group or a trityl group, a method may be employed wherein the compound is treated with an acid such as acetic acid, formic acid, trifluoroacetic acid or hydrochloric acid, preferably within a temperature range of from $-20°$ C. to $50°$ C. for from 10 minutes to 24 hours in the absence of a solvent or usually in an inert solvent such as methylene chloride, anisole, tetrahydrofuran, methanol or ethanol or a solvent mixture thereof with water.

For example, when the protecting group is a benzyl group, a benzhydryl group or a trityl group, a method may be employed wherein the compound is catalytically reduced with a catalyst such as a palladium-carbon catalyst or a Raney nickel catalyst preferably under a hydrogen pressure of from 1 to 20 kg/cm$^2$ preferably within a temperature range of from $0°$ C. to $40°$ C. for from 10 minutes to 24 hours usually in an inert solvent such as methanol, ethanol, dioxane, water or acetic acid, or a solvent mixture thereof.

Among compounds represented by general formula (III-a), an optically active compound represented by general formula (III-1b):

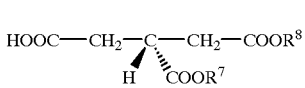

or general formula (III-2b):

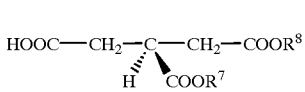

[wherein each of $R^7$ and $R^8$ which are the same or different, is a carboxyl-protecting group] can be obtained by reacting a racemic mixture of the compound represented by general formula (III-b):

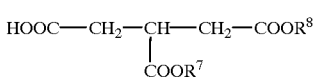

[wherein each of $R^7$ and $R^8$ which are the same or different, is a carboxyl-protecting group] with cinchonidine or quinine to obtain a mixture of two diastereomers, then separating and collecting either one of the diastereomers by utilizing the difference in the solubility between the two diastereomers, followed by recovering the free carboxylic acid by treating with an acid.

Separation of the diastereomer mixture may be conducted in an organic solvent such as carbon tetrachloride or isopropyl ether. Usually, the mixture of the diastereomers is dissolved in a solvent in a hot state, and the solution is gradually cooled to utilize the solubility difference for separation of the diastereomers.

Further, either one of the diastereomers thus obtained is treated with an acid such as hydrochloric acid to obtain an optically active compound represented by general formula (III-1b) or (III-2b).

The compounds represented by general formula 19 and 20 may be commercially available or can be produced by a proper combination, as the case requires, of the methods disclosed in Reference Examples, or conventional methods or methods similar thereto.

Process I

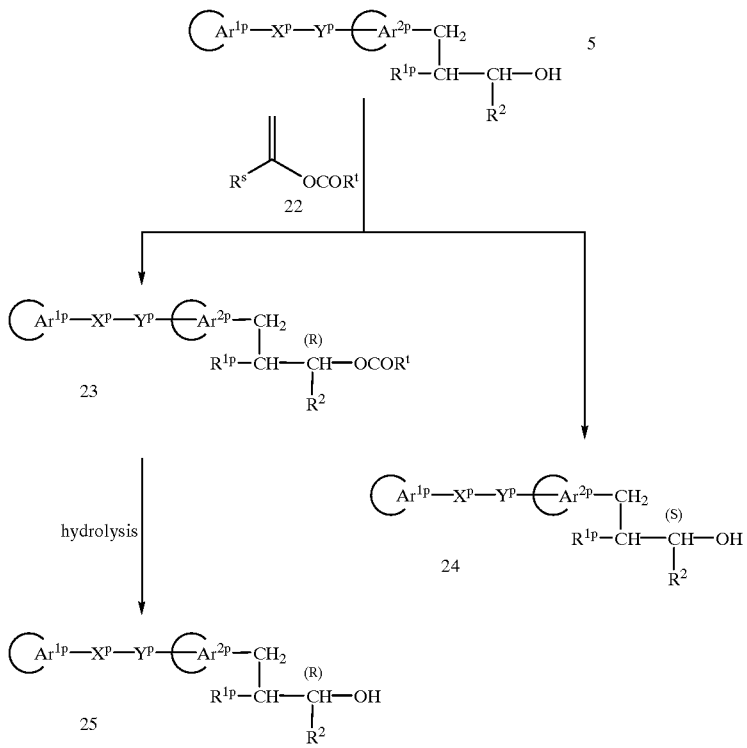

[wherein $R^s$ is a hydrogen atom or a methyl group; $R^t$ is a lower alkyl group, an aryl group or an aralkyl group; and

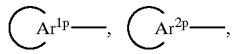

$R^{1p}$, $R^2$, $X^p$ and $Y^p$ are the same as defined above]

Process I is a process for preparing an optically active substance 24 or 25 of a compound represented by general formula 5.

According to this process, the desired optically active alcohol compounds 24 and 25 can be prepared by reacting a vinyl ester derivative represented by general formula 22 to a racemic alcohol derivative represented by general formula 5 in the presence of a lipase, separating the obtained optically active ester derivative 23 and the optically active alcohol derivative, and then hydrolyzing the ester group with respect to the optically active ester derivative 23.

$R^t$ of the vinyl ester derivative represented by general formula 22 is preferably a lower alkyl group such as a methyl group or an ethyl group; an aryl group such as a phenyl group or a naphthyl group; or an aralkyl group such as a benzyl group or a 2-phenylethyl group. Particularly preferred is a methyl group, i.e. a case wherein the compound represented by general formula 22 is vinyl acetate or isopropenyl acetate.

The above optical resolution reaction by lipase can be conducted usually in an inert solvent such as methylene chloride, chloroform, ethyl ether, tetrahydrofuran, benzene, toluene, hexane, heptane or acetonitrile, or by using the starting material vinyl ester derivative represented by general formula 22 itself as the solvent.

The vinyl ester derivative 22 is used usually in an amount of 1 mol or in a large excess molar amount, preferably from 1 to 100 mols, per mol of the starting material compound 5, and the amount of the lipase as the catalyst is from 0.01 to 100%, preferably from 0.1 to 20%, by weight, relative to the compound 5.

The type of the lipase is preferably a lipase derived from Pseudomonas sp. such as Toyothium LIP™ (manufactured by Toyobo).

Further, the above enzymatic reaction tends to be accelerated, when the reaction is carried out in the presence of a base. As a base to be used for this purpose, an organic base such as triethylamine or diisopropylethylamine, is preferred.

The base is used usually in an amount of 0.01 mol or a slightly excess molar amount, preferably from 0.1 to 1.5 mols, relative to the starting material compound 5.

The reaction temperature is usually from 0° C. to 50° C., preferably from room temperature to 40° C. The reaction time is usually from 30 minutes to 7 days, preferably from 1 hour to 48 hours.

The hydrolytic reaction of the ester represented by general formula 23 can be conducted by a common method well known in the synthetic organic chemistry under an acidic or basic condition.

Pharmacological Test 1 (Inhibitory Activities Against Protein-Farnesyl Transferase)

To demonstrate the usefulness of the present invention, 50% inhibitory concentrations ($IC_{50}$ values) of the compounds of the present invention against the protein-farnesyl transferase (PFT) activities, were obtained.

(1) Preparation of PFT

PFT was separated in such a manner that a soluble fraction of rat's brain was fractionated by means of 30%–50% saturated ammonium sulfate, further dialyzed and then subjected to column chromatography by Q-sepharose™ (manufactured by Pharmacia) (Reiss et al., Cell, vol. 62, pp. 81–88 (1990)).

(2) Method for Measuring PFT Activities

Measurement of PFT activities was conducted by using, as a prenyl acceptor, H-ras protein or a peptide corresponding to the C-terminal 7 amino acid residues of K-rasB protein which had biotin added to the N-terminal (biotin-added Lys-Thr-Ser-Cys-Val-Ile-Met) and, as a prenyl donor, [$^3$H]-labeled farnesyl pyrophosphate (FPP) (Reiss et al., Methods: A companion to Methods in Enzymology, vol. 1, No. 3, pp. 241–245 (1990)).

The [$^3$H]-labeled farnesyl pyrophosphate (22.5 Ci/mmol) was purchased from New England Nuclear Co. Non-labeled farnesyl pyrophosphate was chemically synthesized from ditrethylammonium phosphate, trans-trans-farnesol and trichloroacetonitrile and purified by a XAD-2-resin column and diethylaminoethylcellulose (Cornforth et al., Methods in Enzymology, vol. 15, pp. 385–390 (1969)).

H-ras protein was expressed in *Escherichia coli* and purified (Gibbs et al., Proc. Natl. Acad. Sci., vol. 81, pp. 5704–5708 (1984)).

The PFT reaction solution containing H-ras protein as the prenyl acceptor was 25 μl, and its composition was 50 mM Hepes pH7.5/50 μM ZnCl$_2$/5 mM MgCl$_2$/20 mM KCl/5 mM DDT/0.6 μM all trans [$^3$H]-farnesyl pyrophosphate/25 μM H-ras protein/PFT derived from rat brain (Q-sepharose fraction). The reaction temperature was 37° C., the preincubation time was 10 minutes, and the reaction time was 20 minutes.

The PFT reaction solution containing biotin-added Lys-Thr-Ser-Cys-Val-Ile-Met as the prenyl acceptor, was 25 μl, and its composition was 50 mM tris-Cl pH7.5/50 μM ZnCl$_2$/5 mM MgCl$_2$/20 mM KCl/1 mM DTT/0.2% n-octyl-β-D-glucopyranoside/0.6 μM all trans [$^3$H]-farnesyl pyrophosphate/3.6 μM biotin-added Lys-Thr-Ser-Cys-Val-Ile-Met/PFT derived from rat brain (Q-sepharose fraction). The reaction temperature was 37° C., the preincubation time was 10 minutes, and the reaction time was 20 minutes.

The enzymatic reaction product containing H-ras protein as the prenyl acceptor, was analyzed by SDS-PAGE (sodium dodecyl sulfate/polyacrylamide gel electrophoresis). The [$^3$H]-labeled enzymatic reaction product was boiled for 3 minutes in a buffer solution contain 2% SDS/50 mM Tris-Cl pH6.8/10% sucrose/5% 2-mercaptoethanol, then subjected to 12% polyacrylamide slab get electrophoresis whereby the [$^3$H]-labeled H-ras protein was fluorography-enhanced by EN$^3$HANCE™ (manufactured by New England Nuclear Co.) and then visualize by autoradiography (James et al., Science, vol. 260, No. 25, pp. 1937–1942 (1993)).

The measurement of PFT activities using H-ras protein as the prenyl receptor, was also analyzed by a rapid separate method. The mixed solution for measurement wherein no prenyl donor was present, was preincubated, and a prenyl group transferring reaction was initiated by an addition of [$^3$H]-FPP and terminated at an appropriate time by an addition of 0.5 ml of 4% SDS. Further, 0.5 ml of 30% trichloroacetic acid was added thereto and thoroughly mixed. Then, the reaction solution was left to stand at 4° C. for 60 minutes to let H-ras protein precipitate. This reaction solution was filtered under reduced pressure through a Whatman GF/B filter. The filter was washed 6 times with 2 ml of 6% trichloroacetic acid, and mixed with 8 ml of scintillation cocktail (Clearsol I™, manufactured by Nacalai Tesque Co.). Then, counting was carried out by a Beckmann TRI-CARB2500TR scintillation counter.

Measurement of PFT activities was also carried out by using biotin-added Lys-Thr-Ser-Cys-Val-Ile-Met as the prenyl acceptor. The mixed solution for measurement containing biotin-added Lys-Thr-Ser-Cys-Val-Ile-Met as the prenyl acceptor and containing no prenyl donor, was preincubated, and then a prenyl group transferring reaction was initiated by an addition of [$^3$H]-FPP and terminated at an appropriate time by an addition of 0.2 ml of 2 mg/ml bovine serum albumin/2% sodium dodecyl sulfate/150 mM NaCl. Further, 0.02 ml of avidin agarose (Pierce) was added thereto, and the mixture was shaked for 30 minutes to let the [$^3$H]farnesyl group-transferred biotin-added Lys-Thr-Ser-Cys-Val-Ile-Met sufficiently bond to the avidin agarose. Then, the avidin agarose was washed four times with 1 ml of 2 mg/ml bovin serum albumin (BSA)/4% sodium dodecyl sulfate/150 mM NaCl, and mixed with 1 ml of scintillation cocktail (Clearsol I™, manufactured by Nacalai Tesque). Then, counting was carried out by a Beckmann TRI-CARB2500TR scintillation counter.

The biotin-added Lys-Thr-Ser-Cys-Val-Ile-Met heptapeptide used as an artificial substrate, was synthesized in a solid phase by an Applied biosystems model 431A peptide synthesizer, and an α-amino terminal of the solid phase Lys-Thr-Ser-Cys-Val-Ile-Met heptapeptide which was bound to a resin, was biotin-modified by N-hydroxysuccinimide biotin, then cut off from the resin and purified by reversed phase high performance liquid chromatography (HPLC).

The addition of the compound of the present invention to the PFT reaction system was carried out by preliminarily adding dimethyl sulfoxide in an amount of 1% by volume (0.25 μl) of the reaction solution.

The 50% inhibitory concentrations (IC$_{50}$ values) of the compounds of the present invention against PFT activities, are shown in Table 1.

TABLE 1

| 50% inhibitory concentrations against PFT activities | |
|---|---|
| Compound | IC$_{50}$ (nM) |
| Example 2 | 3.1 |
| Example 4 | 7.8 |

From the foregoing results, the compounds of the present invention have excellent inhibitory activities against protein-farnesyl transferase (PFT) and thus useful as anti-tumor agents, for example, against colon cancer, pancreatic cancer, myloid leukemia, lung cancer, carcinoma cutaneum or thyroid gland cancer, particularly against pancreatic cancer.

Further, the protein-farnesyl transferase (PFT) inhibitor of the present invention is capable of inhibiting transfection of ras and capable of inhibiting reactivation of HIV gene transformed into the host cells, and thus is useful also as an anti-HIV agent.

The compound represented by general formula (I) of the present invention can be orally or parenterally administered, and it may be formulated into a formulation suitable for such administration, so that it can be used as an antitumor agent or an anti-HIV agent. To use the compound of the present invention for clinical purpose, it may be formulated into various formulations by an addition of pharmaceutically acceptable additives to meet the type of administration and then administered. As such additives, various additives which are commonly used in the field of drug formulations, may be used, including, for example, gelatin, lactose, saccharose, titanium oxide, starch, crystalline cellulose, hydroxypropylmethylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbital, sorbitan fatty acid ester, polysorbate, sucrose fatty acid ester, polyoxyethylene hardened castor oil, polyvinylpyrrolidone, magnesium stearate, light silicic anhydride, talc, vegetable oil, benzyl alcohol, gum arabic, propylene glycol, polyalkylene glycol, cyclodextrin and hydroxypropylcyclodextrin, etc.

A drug formulation to be prepared as a mixture with such additives, may, for example, be a solid formulation such as a tablet, a capsule, a granule, a powder or a suppository; or a liquid formulation such as a syrup, an elixir or an injection drug. These formulations can be prepared in accordance with conventional methods commonly employed in the field of drug formulations. Further, in the case of a liquid formulation, it may be of the type which is to be dissolved or suspended in water or in other suitable medium at the time of its use. Particularly, in the case of an injection drug, it may be dissolved or suspended in a physiological saline or in a glucose solution, and a buffering agent or a preserving agent may further be added.

These formulations may contain the compound of the present invention in a proportion of from 1.0 to 100 wt %, preferably from 1.0 to 60 wt % of the total amount. These formulations may further contain other therapeutically effective compounds.

When the compound of the present invention is used as an antitumor agent or an anti-HIV agent, its dose and the frequency of administration vary depending upon the sex, the age, the body weight and the diseased degree of the patient and the type and the range of the intended treating effects. However, in the case of an oral administration, it is preferred to administer from 0.01 to 20 mg/kg per day for an adult all at once or in a few times in a divided fashion. In the case of parenteral administration, it is preferred to administer from 0.002 to 10 mg/kg per day for an adult all at once or in a few times in a divided fashion.

The other therapeutically effective compounds may, for example, be drugs which bring about a decrease of farnesyl pyrophosphate in vivo.

The drugs which bring about a decrease of farnesyl pyrophosphate in vivo, are not particularly limited so long as they are drugs having such activities and which are acceptable as pharmaceuticals. However, biosynthesis-inhibitors against farnesyl pyrophosphate, for example, preferred. Among them, drugs which inhibit the biosynthesis of farnesyl pyrophosphate, such as hydroxymethylglutaryl CoA synthase-inhibitors or hydroxymethylglutaryl CoA reductate-inhibitors represented by e.g. lovastatin, simvastatin, pravastatin and fluvastatin disclosed, for example, in Nature, vol. 343, pp. 425–430 (1990), are preferred. Particularly preferred are hydroxymethylglutaryl CoA reductase-inhibitors such as lovastatin, simvastatin, pravastatin and fluvastatin.

The composition comprising the compound of the present invention and the above drug, can be formulated in the same manner as in the case where the compound of the present invention is used as a single drug. Such a formulation may contain the protein-farnesyl transferase inhibitor and a drug which brings about a decrease of farnesyl pyrophosphate in vivo, as active ingredients, in an amount of from 1.0 to 100 wt %, preferably from 1.0 to 60 wt %, of the entire drug.

Further, the weight ratio of the protein-farnesyl transferase inhibitor and the drug which brings about a decrease of farnesyl pyrophosphate in vivo, may be from 0.001:1 to 1000:1. However, the weight ratio is particularly preferably from 0.01:1 to 100:1.

BEST MODE FOR CARRYING OUT THE INVENTION

Now, the present invention will be described in further detail with reference to Examples and Reference Examples, but the present invention is by no means restricted by such Examples.

EXAMPLE 1

Preparation of 3-(ethoxycarbonyl)-4-hydroxy-4-[N-[(1RS,2RS)-2-(methoxycarbonyl)-1-methyl-3-{5-(phenylcarbamoyl)-2-furyl}propyl]-N-(2-naphthylmethyl)carbamoyl]-3-butenoic Acid (1) Preparation of N-(2-naphthylmethyl)-{(1RS,2RS)-2-(methoxycarbonyl)-1-methyl-3-{5-(phenylcarbamoyl)-2-furyl}propylamine hydrochloride 180 mg of (2RS,3RS)-3-{N-(tert-butoxycarbonyl)-N-(2-naphthylmethyl)amino}-2-{5-(phenylcarbamoyl)-2-furylmethyl}butanoic acid prepared in Reference Example 1 in 5 ml of ethyl acetate was stirred together with a slight excess of diazomethane in ethyl ether for 5 minutes. The reaction solution was evaporated to dryness under reduced pressure, and the residue was dissolved in 5 ml of 4N hydrochloric acid-dioxane and stirred at room temperature for 1 hour. The reaction solution was evaporated to dryness under reduced pressure again, and the residue was purified by silica gel column chromatography [hexane/ethyl acetate= 1/1] to give 140 mg (yield: 92%) of the title compound as a colorless oily substance.

(2) Preparation of tert-butyl 3-)ethoxycarbonyl)-4-[N-[(1RS,2RS)-2-(methoxycarbonyl)-1-methyl-3-{5-(phenylcarbamoyl)-2-furyl}propyl]-N-(2-naphthylmethyl)carbamoyl]-4-(methoxymethyloxy)-3-butenoate 163 mg of 1-benzyl 3-tert-butyl 2-ethyl 1-(methoxymethyloxy)-1-propene-1,2,3-tricarboxylate prepared in Reference Example 5 and 1 ml of 1,4-cyclohexadiene were dissolved in 10 ml of ethanol and refluxed under heating with 100 mg of a 10% palladium-carbon catalyst for 20 minutes. The catalyst was separated by filtration through celite, and the filtrate was evaporated to dryness under reduced pressure to give 129 mg of 3-tert-butyl 2-ethyl 1-(methoxymethyloxy)-1-propene-1,2,3-tricarboxylate as a pale brown oily substance.

129 mg of the carboxylate thus obtained, 140 mg of N-(2-naphthylmethyl)-{(1RS,2RS)-2-(methoxycarbonyl)-1-methyl-3-{5-phenylcarbamoyl)-2-furyl}propylamine hydrochloride [the compound prepared in Example 1(1)] and 255 μl of triethylamine were dissolved in 3 ml of chloroform, and 104 mg of 2-chloro-1,3-dimethylimidazolinium chloride in 2 ml of chloroform was added under cooling with ice. The resulting solution was stirred at the same temperature for 2 hours. The reaction solution was poured into water and extracted with ethyl acetate. The organic layer was dried over anhydrous magnesium sulfate. The desiccant was filtered off, and the solvent was distilled off under reduced pressure. The residue was purified by silica gel thin layer chromatography [Kieselgel™ 60F$_{254}$, Art™5717; hexane/ethyl acetate=½] to give 196 mg (yield: 84% of the title compound as a white solid.

(3) Preparation of 3-(ethoxycarbonyl)-4-hydroxy-4-[N-[(1RS,2RS)-2-(methoxycarbonyl)-1-methyl-3-{5-(phenylcarbamoyl)-2-furyl}propyl]-N-(2-naphthylmethyl)carbamoyl]-3-butenoic acid 30 mg of tert-butyl 3-(ethoxycarbonyl)-4-[N-[(1RS,2RS)-2-(methoxycarbonyl)-1-methyl-3-{5-(phenylcarbamoyl)-2- furyl}propyl]-N-(2-napthylmethyl)carbamoyl]-4-(methoxymethyloxy)-3-butenoate in 0.5 ml of chloroform was stirred with 52 μl of bromotrimethylsilane at −30° C. for 30 minutes and then at 0° C. for 5 hours. After addition of 1N hydrochloric acid, the reaction solution was extracted with ethyl acetate. The organic layer was dried over anhydrous magnesium sulfate, and the desiccant was filtered off. The solvent was distilled off under reduced pressure, and the residue was purified by silica gel thin layer chromatography [Kieselgel™ 60F$_{254}$, Art™5744; chloroform/methanol=9/1] to give 25 mg (yield: 98%) of the title compound as a white solid.

$^1$H-NMR(CDCl$_3$)δ:1.10–1.40(6H,m), 2.55–3.70(8H,m), 4.00–4.90(6H,m), 5.50–5.60 and 5.95–6.05(total 1H, each m), 6.75–7.70(13H,m), 7.92–8.40(1H,m).

FAB-MS:657(M+H)

EXAMPLE 2

Preparation of 3-(ethoxycarbonyl)-4-hydroxy-4-[N-[(1RS,2RS)-2-(isopropoxycarbonyl)-1-methyl-3-{5-(phenylcarbamoyl)-2-furyl}propyl]-N-(2-naphthylmethyl)carbamoyl]-3-butenoic acid (1) Preparation of N-(2-naphthylmethyl)-{(1RS,2RS)-2-(isopropoxycarbonyl)-1-methyl-3-{5-(phenylcarbamoyl)-2-furyl}propylamine hydrochloride 35 mg of (2RS,3RS)-3-{N-(tert-butoxycarbonyl)-N-(2-naphthylmethyl)amino}-2-{5-(phenylcarbamoyl)-2-furylmethyl}butanoic acid prepared in Reference Example 1, 5.8 mg of isopropyl alcohol and 7.9 mg of 4-dimethylaminopyridine were dissolved in 1 ml of chloroform and stirred together with 25 mg of 1-ethyl-3-(3-dimethylaminopropyl)carbodiimide hydrochloride at room temperature for 16 hours. The reaction solution was diluted with ethyl acetate and washed with 1N hydrochloric acid, saturated aqueous sodium hydrogen carbonate and saturated aqueous sodium chloride successively, and the organic layer was dried over anhydrous magnesium sulfate. The desiccant was filtered off, and the solvent was distilled off under reduced pressure. The residue was purified by silica gel thin layer chromatography [Kieselgel™ 60F$_{254}$, Art™5744; hexane/ethyl acetate=1/1], and 30 mg of the resulting compound was dissolved in 1 ml of 4N hydrochloric acid-dioxane and stirred at room temperature for 1.5 hours. The reaction solution was evaporated to dryness under reduced pressure to give 25 mg (yield: 80%) of the title compound as a colorless oily substance.

(2) Preparation of 3-(ethoxycarbonyl)-4-hydroxy-4-[N-[(1RS,2RS)-2-(isopropoxycarbonyl)-1-methyl-3-{5-(phenylcarbamoyl)-2-furyl}propyl]-N-(2-naphthylmethyl)carbamoyl]-3-butenoic acid The reactions in Example 1(2) and (3) were carried out by using N-(2-naphthylmethyl)-{(1RS,2RS)-2-(isopropoxycarbonyl)-1-methyl-3-{5-(phenylcarbamoyl)-2-furyl}propylamine hydrochloride instead of N-(2-naphthylmethyl)-{(1RS,2RS)-2-(methoxycarbonyl)-1-methyl-3-{5-(phenylcarbamoyl)-2-furyl}propylamine hydrochloride used as the starting material in Example 1(2), to give the title compound.

$^1$H-NMR(CDCl$_3$)δ:1.00–1.30(12H,m), 2.55–3.80(5H,m), 4.00–4.95(7H,m), 5.55–5.70 and 5.95–6.05(total 1H, each m), 6.80–7.80(13H,m), 7.90–8.40(1H,m).

FAB-MS:6.85(M+H)

EXAMPLE 3

Preparation of 3-(ethoxycarbonyl)-4-[N-[(1RS,2RS)-2-(ethoxycarbonyl)-1-methyl-3-{5-(phenylcarbamoyl)-2-furyl}propyl]-N-(2-naphthylmethyl)carbamoyl]-4-hydroxy-3-butenoic acid The title compound was prepared in the same manner as in Example 2 except that ethanol was used instead of isopropyl alcohol.

$^1$H-NMR(CDCl$_3$)δ:1.00–1.30(9H,m), 2.70–4.40 and 4.50–5.00(total 13H, each m), 5.70–6.20(1H,m), 6.80–8.00 (13H,m).

FAB-MS:671(M+H)

EXAMPLE 4

Preparation of 3-(ethoxycarbonyl)-4-[N-(1RS,2RS), 3E)-4-(ethoxycarbonyl)-1-methyl-2-{5-(phenylcarbamoyl)-2-furylmethyl}-3-butenyl]-N-(2-naphthylmethyl)carbamoyl]-4-hydroxy-3-butenoic acid (1) Preparation of tert-butyl 3-(ethoxycarbonyl)-4-[N-[(1RS,2RS)-2-(hydroxymethyl)-1-methyl-3-{5-(phenylcarbamoyl)-2-furyl}propyl]-N-(2-naphthylmethyl)carbamoyl]-4-(methoxymethyloxy)-3-butenoate 400 mg of tert-butyl 3-(ethoxycarbonyl)-4-[N-[(1RS,2RS)-2-(tert-butyldimethylsilyloxymethyl)-1-methyl-3-{5-(phenylcarbamoyl)-2-furyl}propyl]-N-(2-naphthylmethyl)carbamoyl]-4-methoxymethyloxy-3-butenoate prepared by the same reaction as in Example 1(2) by using N-(2-naphthylmethyl)-[(1RS,2RS)-2-(tert-butyldimethylsilyloxymethyl)-1-methyl-3-{5-(phenylcarbamoyl)-2-furyl}propyl]amine prepared in Reference Example 4 was dissolved in 4 ml of tetrahydrofuran and stirred together with 0.95 ml of 1.0M tetrabutylammonium fluoride in tetrahydrofuran solution at room temperature for 2 hours. The reaction solution was poured into water and extracted with ethyl acetate, and the organic layer was washed with saturated aqueous ammonium chloride and saturated aqueous sodium chloride and dried over anhydrous magnesium sulfate. The desiccant was filtered off, and the solvent was distilled off under reduced pressure. The residue was purified by column chromatography [hexane/ethyl acetate=1/1] to give 147 mg (yield: 43%) of the title compound as a colorless oily substance.

(2) Preparation of tert-butyl 3-(ethoxycarbonyl)-4-[N-[(1RS,2RS)-2-formyl-1-methyl-3-{5-(phenylcarbamoyl)-2-furyl}propyl]-N-(2-naphthylmethyl)carbamoyl]-4-(methoxymethyloxy)-3-butenoate 124 mg of tert-butyl 3-(ethoxycarbonyl)-4-[N-[(1RS,2RS)-2-(hydroxymethyl)-1-methyl-3-{5-(phenylcarbamoyl)-2-furyl}propyl]-N-(2-naphthylmethyl)carbamoyl]-4-(methoxymethyloxy)-3-butenoate was dissolved in 3 ml of chloroform and stirred with 288 mg of the Dess-Martin reagent (periodinane) at room temperature for 30 minutes. The reaction solution was poured into a mixture of saturated aqueous sodium hydrogencarbonate and saturated aqueous sodium thiosulfate and extracted with ethyl acetate. The organic layer was washed with saturated aqueous sodium chloride and dried over anhydrous magnesium sulfate. The desiccant was filtered off, and the solvent was distilled off under reduced pressure. The residue was purified by silica gel thin layer chromatography [Kieselgel™ 60F$_{254}$, Art™5744; hexane/ethyl acetate=1/2] to give 65 mg (yield: 53%) of the title compound as a white solid.

(3) Preparation of tert-butyl 3-(ethoxycarbonyl)-4-[N-[(1RS,2RS,3E)-4-(ethoxycarbonyl-1-methyl-2-{5-(phenylcarbamoyl)-2-furylmethyl}-3-butenyl]-N-(2-naphthylmethyl)carbamoyl]-4-(methoxymethyloxy)-3-butenoate 17 mg of tert-butyl 3-(ethoxycarbonyl)-4-[N-[(1RS,2RS)-2-formyl-1-methyl-3-{5-(phenylcarbamoyl)-2-furyl}propyl]-N-(2-naphthylmethyl)carbamoyl]-4-

(methoxymethyloxy)-3-butenoate and 12 mg of (carboethoxymethylene)triphenylphosphorane were dissolved in 1 ml of chloroform and stirred at room temperature for 3 days. The solvent was distilled off under reduced pressure, and the residue was purified by silica gel thin layer chromatography [Kieselgel™ 60F$_{254}$, Art™5744; hexane/ethyl acetate=1/1] to give 16 mg (yield: 85%) of the title compound as a colorless oily substance.

(4) Preparation of 3-(ethoxycarbonyl)-4-[N-[(1RS,2RS,3E)-4-(ethoxycarbonyl)-1-methyl-2-{(5-(phenylcarbamoyl)-2-furylmethyl}-3-butenyl]-N-(2-naphthylmethyl)carbamoyl]-4-hydroxy-3-butenoic acid The title compound was prepared by the same reaction as in Example1(3) by using tert-butyl 3-(ethoxycarbonyl)-4-[N-[(1RS,2RS,3E)-4-ethoxycarbonyl-1-methyl-2-{5-(phenylcarbamoyl)-2-furylmethyl}-3-butenyl]-N-(2-naphthylmethyl)carbamoyl]-4-(methoxymethyloxy)-3-butenoate as the starting material.

$^1$H-NMR(CDCl$_3$)δ:1.10–1.40(9H,m), 2.40–3.70(5H,m), 3.90–4.90(8H,m), 5.53–5.78 and 5.90–6.03(total 2H, each m), 6.48–6.85(1H,m), 6.90–7.80(13H,m), 7.90–8.52(1H,m).

FAB-MS:697(M+H)

EXAMPLE 5

Preparation of 3-(tert-butoxycarbonyl)-4-[N-[(1RS,2RS)-2-(tert-butoxycarbonyl)-1-methyl-3-{5-(phenylcarbamoyl)-2-furyl}propyl]-N-{(E)-3-phenyl-2-propenyl}carbamoyl]-4-hydroxy-3-butenoic acid (1) Preparation of tert-butyl (2RS,3RS)-2-[N-[(1RS,2RS)-2-(tert-butoxycarbonyl)-1-methyl-3-{5-(phenylcarbamoyl)-2-furyl}propyl]-N-{(E)-3-phenyl-2-propenyl}carbamoyl]-5-oxotetrahydrofuran-3-carboxylate 86 mg of tert-butyl (2RS,3RS)-2-{5-(phenylcarbamoyl)-2-furylmethyl}-3-{(E)-3-phenyl-2-propenylamino}butanoate prepared in Reference Example 3, 46 mg of (2RS,3RS)-3-(tert-butoxycarbonyl)-5-oxotetrahydrofuran-2-carboxylic acid prepared in Reference Example 6 and 140 μl of triethylamine were dissolved in 2 ml of chloroform and stirred with 41 mg of 2-chloro-1,3-dimethylimidazolinium chloride in 1 ml of chloroform under cooling with ice for 10 minutes and then at room temperature for 1 hour. The reaction solution was poured into water and extracted with ethyl acetate, and the organic layer was dried over anhydrous magnesium sulfate. The desiccant was filtered off, and the solvent was distilled off under reduced pressure. The residue was purified by silica gel column chromatography [hexane/ethyl acetate=10/1→2/1] to give 124 mg (stoichiometric yield) of the title compound as a colorless oily substance.

(2) Preparation of methyl (3RS,4RS)-3-(tert-butoxycarbonyl)-4-[N-[(1RS,2RS)-2-(tert-butoxycarbonyl)-1-methyl-3-{5-(phenylcarbamoyl)-2-furyl}propyl]-N-{(E)-3-phenyl-2-propenyl}carbamoyl]-4-hydroxybutanoate 104 mg of tert-butyl (2RS,3RS)-2-[N-[(1RS,2RS)-2-(tert-butoxycarbonyl)-1-methyl-3-{5-(phenylcarbamoyl)-2-furyl}propyl]-N-{(E)-3-phenyl-2-propenyl}carbamoyl]-5-oxotetrahydrofuran-3-carboxylate was dissolved in a mixture of 3 ml of tetrahydrofuran and 1 ml of water and stirred together with 1.0 ml of 1N aqueous sodium hydroxide at room temperature for 18 hours. The reaction solution was acidified with 1N hydrochloric acid and extracted with ethyl acetate. The organic layer was dried over anhydrous magnesium sulfate. The desiccant was filtered off, and the solvent was distilled off under reduced pressure. The resulting carboxylic acid was dissolved in 10 ml of ethyl acetate, and a slight excess of diazomethane in ethyl ether was added at room temperature. The solvent was distilled off under reduced pressure, and the residue was purified by silica gel column chromatography [hexane/ethyl acetate=10/1→2/1] to give 109 mg (stoichiometric yield) of the title compound as a colorless oily substance.

(3) Preparation of methyl 3-(tert-butoxycarbonyl)-4-[N-[(1RS,2RS)-2-(tert-butoxycarbonyl)-1-methyl-3-{5-(phenylcarbamoyl)-2-furyl}propyl]-N-{(E)-3-phenyl-2-propenyl}carbamoyl]-4-hydroxy-3-butenoate 92 mg of methyl (3RS,4RS)-3-(tert-butoxycarbonyl)-4-[N-[(1RS,2RS)-2-(tert-butoxycarbonyl)-1-methyl-3-{5-(phenylcarbamoyl)-2-furyl}propyl]-N-{(E)-3-phenyl-2-propenyl}carbamoyl]-4-hydroxybutanoate was dissolved in 3 ml of acetonitrile and stirred with 56 mg of tetrapropylammonium perruthenate at room temperature for 2 hours. The solvent was distilled off under reduced pressure, and the residue was roughly purified by silica gel short column chromatography [chloroform→methanol] and purified again by silica gel column chromatography [hexane/ethyl acetate=2/1→3/2] to give 70 mg (yield: 76%) of the title compound as a colorless oily substance.

(4) Preparation of 3-(tert-butoxycarbonyl)-4-[N-[(1RS,2RS)-2-(tert-butoxycarbonyl)-1-methyl-3-{5-(phenylcarbamoyl)-2-furyl}propyl]-N-{(E)-3-phenyl-2-propenyl}carbamoyl]-4-hydroxy-3-butenoic acid 68 mg of methyl 3-(tert-butoxycarbonyl)-4-[N-[(1RS,2RS)-2-(tert-butoxycarbonyl)-1-methyl-3-{5-(phenylcarbamoyl)-2-furyl}propyl]-N-{(E)-3-phenyl-2-propenyl}carbamoyl]-4-hydroxy-3-butenoate was dissolved in a mixture of 3 ml of tetrahydrofuran and 1 ml of water and stirred together with 1 ml of 1N aqueous sodium hydroxide at room temperature for 40 hours. The reaction solution was acidified with 1N hydrochloric acid and extracted with ethyl acetate. The organic layer was dried over anhydrous magnesium sulfate. The desiccant was filtered off, and the solvent was distilled off under reduced pressure. The residue was purified by silica gel column chromatography [chloroform/methanol=20/1→10/1] to give 44 mg (yield: 66%) of the title compound as a pale yellow solid.

$^1$H-NMR(CDCl$_3$)δ:1.10–1.50(21H,m), 2.80–3.50 and 3.60–4.65(total 9H, each m), 6.05–6.45 and 6.50–6.65(total 3H, each m), 7.00–7.40(9H,m), 7.65–7.80(2H,m), 7.95–8.60 (1H,m).

FAB-MS:703(M+H)

REFERENCE EXAMPLE 1

Preparation of (2RS,3RS)-3-{N-tert-butoxycarbonyl)-N-(2-naphthylmethyl)amino}-2-{5-(phenylcarbamoyl)-2-furylmethyl}butanoic acid (1) Preparation of tert-butyl 2-{5-(ethoxycarbonyl)-2-furylmethyl}-3-oxobutanoate A solution of 1.78 g of potassium tert-butoxide in 60 ml of tert-butyl alcohol was stirred together with 3.00 g of tert-butyl acetoacetate at 60° C. for 30 minutes under heating and then cooled to room temperature. 3.40 g of ethyl 5-(chloromethyl)-2-furancarboxylate was added dropwise, and the solution was stirred at room temperature for 16 hours. The reaction solution was poured into water and extracted with ethyl acetate, and the organic layer was washed with saturated aqueous sodium chloride and dried over anhydrous magnesium sulfate. The desiccant was filtered off, and the solvent was distilled off under reduced pressure. The residue was purified by silica gel column chromatography [hexane/ethyl acetate=9/1→5/1] to give 2.26 g of the title compound as a colorless oily substance.

(2) Preparation of tert-butyl (2RS,3SR)-2-{5-(ethoxycarbonyl)-2-furylmethyl}-3-hydroxybutanoate To 2.26 g of tert-butyl 2-{5-(ethoxycarbonyl)-2-furylmethyl}-3-oxobutanoate in 50 ml of tetrahydrofuran, 7.7 ml of 1M lithium tri-sec-butylborohydride in tetrahydrofuran solution was added at −78° C. under stirring, and the resulting reaction solution was stirred at the same temperature for 2 hours. After addition of water, the reaction solution was stirred at room temperature for 30 minutes and extracted with ethyl acetate. The organic layer was washed with saturated aqueous sodium chloride and dried over anhydrous magnesium sulfate. The desiccant was filtered off, and the solvent was distilled off under reduced pressure. The residue was purified by silica gel column chromatography [hexane/ethyl acetate=12/1→4/1] to give 1.65 g of the title compound.

(3) Preparation of tert-butyl (2RS,3RS)-3-amino-2-{5-(ethoxycarbonyl)-2-furylmethyl}butanoate To 1.65 g of tert-butyl (2RS,3SR)-2-{5-(ethoxycarbonyl)-2-furylmethyl}-3-hydroxybutanoate in 40 ml of tetrahydrofuran, 2.32 g of triphenylphosphine, 1.40 ml of diethyl azodicarboxylate and 2.43 g of diphenylphosphoryl azide were added successively under cooling with ice under stirring, and the resulting reaction solution was stirred at room temperature for 18 hours. The reaction solution was evaporated to dryness under reduced pressure, and the residue was purified by silica gel column chromatography [hexane/ethyl acetate=12/1→3/1]. The resulting azide was refluxed together with 2.33 g of triphenylphosphine in 33 ml of 10% hydrous tetrahydrofuran under heating for 3 hours. The reaction solution was cooled to room temperature, and the solvent was distilled off under reduced pressure. The residue was purified by silica gel column chromatography [hexane/ethyl acetate=1/1→ethyl acetate/methanol=10/1] to give 686 mg of the title compound as a pale yellow oily substance.

(4) Preparation of tert-butyl (2RS,3RS)-2-{5-(ethoxycarbonyl)-2-furylmethyl}-3-{(2-naphthylmethyl)amino}butanoate 500 mg of tert-butyl (2RS,3RS)-3-amino-2-{5-(ethoxycarbonyl)-2-furylmethyl}butanoate in 15 ml of methanol was stirred together with 251 mg of 2-naphthaldehyde at 50° C. for 2 hours under heating. The reaction solution was cooled to 0° C. and stirred with 61 mg of sodium borohydride at the same temperature for 15 minutes. Ethyl acetate and water were added to the reaction solution for extraction, and the organic layer was washed with saturated aqueous sodium chloride and then dried over anhydrous magnesium sulfate. The desiccant was filtered off, and the solvent was distilled off under reduced pressure. The residue was purified by silica gel column chromatography [hexane/ethyl acetate=6/1] to give 555 mg of the title compound as a colorless oily substance.

(5) Preparation of tert-butyl (2RS,3RS)-3-{(2-naphthylmethyl)amino}-2-{5-(phenylcarbamoyl)-2-furylmethyl}butanoate 538 mg of tert-butyl (2RS,3RS)-2-{5-(ethoxycarbonyl)-2-furylmethyl}-3-{(2-naphthylmethyl)amino}butanoate was dissolved in a mixture of 5 ml of tetraydrofuran and 5 ml of methanol and stirred together with 5 ml of 1N aqueous sodium hydroxide at room temperature for 2 hours. The reaction solution was acidified by 1N hydrochloric acid and then extracted with ethyl acetate. The extract was dried over anhydrous magnesium sulfate. The desiccant was filtered off, and the solvent was distilled off under reduced pressure. The residue was dissolved in 5 ml of dimethylformamide and then stirred together with 219 mg of aniline and 339 mg of 1-ethyl-3-(3-dimethylaminopropyl)carbodiimide hydrochloride at room temperature for 17 hours. After addition of water, the reaction solution was extracted with ethyl acetate, and the organic layer was washed with 1N aqueous sodium hydroxide and saturated aqueous sodium chloride and then dried over anhydrous magnesium sulfate. The desiccant was filtered off, and the solvent was distilled off under reduced pressure. The residue was purified by silica gel column chromatography [hexane/ethyl acetate=3/1] to give 473 mg of the title compound as a colorless foamy substance.

(6) Preparation of (2RS,3RS)-3-{N-(tert-butoxycarbonyl)-N-(2-naphthylmethyl)amino}-2-{5-(phenylcarbamoyl)-2-furylmethyl}butanoate 846 mg of tert-butyl (2RS,3RS)-3-{(2-naphthylmethyl)amino}-2-{5-(phenylcarbamoyl)-2-furylmethyl}butanoate in 20 ml of formic acid was stirred at room temperature for 3 hours, and the formic acid was distilled off under reduced pressure. The residue was dissolved in 20 ml of 4N hydrochloric acid-dioxane and stirred at room temperature for 15 minutes. The reaction solution was evaporated to dryness under reduced pressure to give 814 mg of an amine hydrochloride as a white solid. 814 mg of the amine hydrochloride, 8.5 ml of 1N aqueous sodium hydroxide and 8.5 ml of dioxane were mixed and stirred vigorously together with 1.19 g of di-tert-butyl dicarbonate at room temperature for 18 hours. After addition of 1N hydrochloric acid, the reaction solution was extracted with ethyl acetate, and the organic layer was washed with 1N hydrochloric acid, water and saturated aqueous sodium chloride successively and then dried over anhydrous magnesium sulfate. The desiccant was filtered off, and the solvent was distilled off under reduced pressure. The residue was purified by silica gel column chromatography [chloroform/methanol=50/1] to give 755 mg of the title compound as a white solid.

REFERENCE EXAMPLE 2

Preparation of 2-(chloromethyl)-5-(phenylcarbamoyl) furan (1) Preparation of 5-(phenylcarbamoyl)-2-furfural diethyl acetal To 20.0 g of 2-furfural diethyl acetal in 200 ml of ethyl ether, 75 ml of 1.68M n-butyllithium in hexane solution was added at −78° C. under a nitrogen atmosphere, and the resulting solution was stirred at the same temperature for 30 minutes and then at room temperature for 30 minutes. The reaction solution was cooled to −78° C. again, and 14.0 ml of phenyl isocyanate was added. The reaction solution was stirred at room temperature for 17 hours. After addition of saturated aqueous ammonium chloride, the reaction solution was extracted with ethyl acetate, and the organic layer was washed with 1N hydrochloric acid, water, saturated aqueous sodium hydrogencarbonate and saturated aqueous sodium chloride successively and then dried over anhydrous magnesium sulfate. The desiccant was filtered off, and the solvent was distilled off under reduced pressure. The residue was purified by silica gel column chromatography [hexane/ethyl acetate=10/1→1/1] to give 25.9 g of the title compound as a colorless oily substance.

(2) Preparation of 5-(phenylcarbamoyl)-2-furfural 50 ml of trifluoroacetic acid was added to 25.2 g of 5-(phenylcarbamoyl)-2-furfural diethyl acetal in 200 ml of chloroform under cooling with ice, and the resulting solution was stirred at the same temperature for 3 hours. The reaction solution was diluted with chloroform, then washed with water, saturated aqueous sodium hydrogencarbonate and saturated aqueous sodium chloride successively, and dried over anhydrous sodium sulfate. The desiccant was filtered off, and the solvent was distilled off under reduced pressure. The residue was purified by silica gel column chromatography [hexane/ethyl acetate=10/1→1/1] to give 12.5 g of the title compound as a colorless oily substance.

(3) Preparation of 2-(chloromethyl)-5-)phenylcarbamoyl) furan 3.5 g of sodium borohydride was added to 12.4 g of 5-(phenylcarbamoyl)-2-furfural in 200 ml of methanol under cooling with ice, and the resulting solution was stirred at the same temperature for 10 minutes and then at room temperature for 1 hour. The reaction solution was mixed with water under cooling with ice and stirred at room temperature for 30 minutes. The solvent was distilled off under reduced pressure, and ethyl ether was added to the residue. The resulting solution was washed with 1N hydrochloric acid, water, saturated aqueous sodium hydrogencarbonate and saturated aqueous sodium chloride successively and then dried over anhydrous sodium sulfate. The desiccant was filtered off, and the solvent was distilled off under reduced pressure. The residue was purified by silica gel column chromatography [hexane/ethyl acetate=1/1→1/2] to give 10.3 g of an alcohol.

5.40 g of the alcohol was dissolved in 100 ml of chloroform and 2.0 ml of thionyl chloride was added under cooling at −60° C. The reaction solution was stirred at 0° C. for 1 hour, then mixed with water and extracted with ethyl acetate. The organic layer was washed with water, saturated aqueous sodium hydrogencarbonate and saturated aqueous sodium chloride successively and then dried over anhydrous sodium sulfate. The desiccant was filtered off, and the solvent was distilled off under reduced pressure. The residue was purified by silica gel column chromatography [hexane/ethyl acetate=3/1] to give 4.55 g of the title compound as a colorless oily substance.

REFERENCE EXAMPLE 3

Preparation of tert-butyl (2RS,3RS)-2-{5-(phenylcarbamoyl)-2-furylmethyl}-3-{(E)-3-phenyl-2-propenylamino}butanoate (1) Preparation of tert-butyl 3-oxo-2-{5-(phenylcarbamoyl)-2-furylmethyl}butanoate To 9.6 g of tert-butyl acetoacetate was dissolved in 80 ml of tetrahydrofuran, and 2.33 g of 60% oil sodium hydride was added under cooling with ice under stirring. The resulting solution was stirred at the same temperature for 10 minutes. After addition of 13.6 g of 2-(chloromethyl)-5-(phenylcarbamoyl)furan obtained in Reference Example 2 in 80 ml of tetrahydrofuran, the solution was stirred at room temperature for 10 minutes and then at 60° C. for 13 hours under heating. Water and ethyl acetate were added to the reaction solution for extraction, and the organic layer was washed with water, saturated aqueous sodium hydrogencarbonate and saturated aqueous sodium chloride successively and then dried over anhydrous sodium sulfate. The desiccant was filtered off, and the solvent was distilled off under reduced pressure. The residue was purified by silica gel column chromatography [hexane/ethyl acetate=10/1→3/1] to give 14.0 g of the title compound as a colorless oily substance.

(2) Preparation of tert-butyl (2RS,3SR)-3-hydroxy-2-{5-(phenylcarbamoyl)-2-furylmethyl}butanoate 43 ml of 1M lithium tri-sec-butylborohydride in tetrahydrofuran solution was added to 14.0 g of tert-butyl 3-oxo-2-{5-(phenylcarbamoyl)-2-furylmethyl}butanoate in 100 ml of tetrahydrofuran at −78° C. under stirring, and the resulting reaction solution was stirred at the same temperature for 1 hour. While the reaction solution was cooled with ice under stirring, 50 ml of 4N aqueous sodium hydroxide was added, and then 35 ml of 35% aqueous hydrogen peroxide was gradually added dropwise. The reaction solution was stirred at room temperature for 1 hour. Ethyl ether and water were added to the reaction solution for extraction, and the organic layer was washed with saturated aqueous sodium thiosulfate and saturated aqueous sodium chloride and then dried over anhydrous sodium sulfate. The desiccant was filtered off, and the solvent was distilled off under reduced pressure. The residue was purified by silica gel column chromatography [hexane/ethyl acetate=5/1→1/1] to give 8.44 g of the title compound as a colorless oily substance.

(3) Preparation of tert-butyl (2RS,3RS)-2-{5-(phenylcarbamoyl)-2-furylmethyl}-3-{(E)-3-phenyl-2-propenylamino}butanoate 3.0 g of tert-butyl (2RS,3SR)-3-hydroxy-2-{5-(phenylcarbamoyl)-2-furylmethyl}butanoate in 50 ml of tetrahydrofuran was mixed with 3.25 g of triphenylphosphine, 2.0 ml of diethyl azodicarboxylate and 2.7 ml of diphenylphosphoryl azide under cooling with ice under stirring and then stirred at room temperature for 18 hours. The reaction solution was evaporated to dryness under reduced pressure, and the residue was purified by silica gel column chromatography [hexane/ethyl acetate=10/1→2/1]. The resulting azide was refluxed together with 3.25 g of triphenylphosphine in 55 ml of 10% hydrous tetrahydrofuran for 2 hours under heating. The reaction solution was cooled to room temperature, and the solvent was distilled off under reduced pressure. The residue was purified by silica gel column chromatography [hexane/ethyl acetate=1/1→ethyl acetate→chloroform/methanol=10/1→5/1]. The resulting amine and 1.6 ml of trans-cinnamaldehyde were dissolved in 50 ml of methanol and stirred at 70° C. for 1.5 hours under heating. The reaction solution was cooled to 0° C. and then stirred with 800 mg of sodium borohydride at the same temperature for 15 minutes and then at room temperature for 24 hours. Water was added under cooling with ice, and the reaction solution was stirred at room temperature for 30 minutes. The solvent was distilled off under reduced pressure. The residue was mixed with ethyl ether and washed with 1N hydrochloric acid, water, saturated aqueous sodium hydrogencarbonate and saturated aqueous sodium chloride successively and then dried over anhydrous sodium sulfate. The desiccant was filtered off, and the solvent was distilled off under reduced pressure. The residue was purified by silica gel column chromatography [hexane/ethyl acetate=2/1→1/1] to give 1.05 g of the title compound as a yellow oily substance.

REFERENCE EXAMPLE 4

Preparation of N-(2-naphthylmethyl)-[(1RS,2RS)-2-(tert-butyldimethylsilyloxymethyl)-1-methyl-3-{5-(phenylcarbamoyl)-2-furyl}propyl]amine (1) Preparation of (2RS,3SR)-3-(hydroxymethyl)-4-{5-(phenylcarbamoyl)-2-furyl}butan-2-ol 3.0 g of tert-butyl (2RS,3SR)-3-hydroxy-2-{5-(phenylcarbamoyl)-2-furylmethyl}butanoate [the compound prepared in Reference Example 3(2)] in 30 ml of tetrahydrofuran was stirred together with 1.09 g of lithium borohydride at room temperature for 2 hours. The reaction solution was cooled to 0° C., mixed with 2N hydrochloric acid and extracted with ethyl acetate, and the organic layer was dried over anhydrous magnesium sulfate. The desiccant was filtered off, and the solvent was distilled off under reduced pressure to give 1.56 g of the title compound as a colorless oily substance.

(2) Preparation of (2RS,3SR)-3-(tert-butyldimethylsilyloxymethyl)-4-{5-(phenylcarbamoyl)-2-furyl}butan-2-ol 645 mg of (2RS,3SR)-3-(hydroxymethyl)-4-{5-(phenylcarbamoyl)-2-furyl}butan-2-ol in 12 ml of dimethylformamide was mixed with 305 mg of imidazole and 372 mg of tert-butyldimethylsilyl chloride under cooling with ice and stirred at the same temperature for 1 hour. Saturated aqueous ammonium chloride and ethyl acetate were added to the reaction solution for extraction, and the organic layer was washed with water and saturated aqueous sodium chloride and then dried over anhydrous magnesium sulfate. The desiccant was filtered off, and the solvent was distilled off under reduced pressure. The residue was purified by silica gel column chromatography [hexane/ethyl acetate=3/1] to give 805 mg of the title compound as a colorless oily substance.

(3) Preparation of N-(2-naphthylmethyl)-[(1RS,2RS)-2-(tert-butyldimethylsilyloxymethyl)-1-methyl-3-(5-(phenylcarbamoyl)-2-furyl}propyl]amine The title compound was prepared by the same reactions as in Reference Example 1(3) and (4) by using (2RS,3SR)-3-(tert-butyldimethylsilyloxymethyl)-2-hydroxy-4-{5-(phenylcarbamoyl)-2-furyl}butane instead of tert-butyl (2RS,3SR)-2-{5-(ethoxycarbonyl)-2-furylmethyl}-3-hydroxybutanoate used as the starting material in Reference Example 1(3).

REFERENCE EXAMPLE 5

Preparation of 1-benzyl 3-tert-butyl 2-ethyl 1-(methoxymethyloxy)-1-propene-1,2,3-tricarboxylate (1) Preparation of 3-tert-butyl 1,2-diethyl (1S,2R)-1-hydroxy-1,2,3-propanetricarboxylate 31 ml of 1.69M n-butyllithium in hexane was dissolved in 30 ml of tetrahydrofuran, stirred with 7.1 ml of diisopropylamine under cooling with ice for 30 minutes and then cooled to −78° C. 4.94 g of diethyl (S)-malate in 20 ml of tetrahydrofuran was added dropwise at −50° C. or below, and the reaction solution was stirred at −20° C. for 1.5 hours. The reaction solution was cooled to −78° C., and 5.58 g of tert-butyl bromoacetate and 4.66 g of hexamethylphosphoryl triamide in 20 ml of tetrahydrofuran were added dropwise at −50° C. or below. The reaction solution was stirred at room temperature for 1 hour. The reaction solution was poured into 150 ml of 0.5N hydrochloric acid and extracted with diethyl ether, and the organic layer was washed with saturated aqueous sodium hydrogencarbonate and saturated aqueous sodium chloride and then dried over anhydrous magnesium sulfate. The desiccant was filtered off, and the solvent was distilled off under reduced pressure. The residue was purified by silica gel column chromatography [hexane/ethyl acetate=5/1→4/1] to give 3.88 g of the title compound as a yellow oily substance.

(2) Preparation of 1-benzyl 3-tert-butyl 2-ethyl (1S,2R)-1-hydroxy-1,2,3-propanetricarboxylate 913 mg of 3-tert-butyl 1,2-diethyl (1S,2R)-1-hydroxy-1,2,3-propanetricarboxylate was dissolved in a mixture of 21 ml of tetrahydrofuran and 9 ml of water and stirred with 3 ml of 1N aqueous sodium hydroxide at room temperature for 3 days. The reaction solution was acidified with 1N hydrochloric acid and then extracted with ethyl acetate, and the organic layer was dried over anhydrous magnesium sulfate.

The desiccant was filtered off, and the solvent was distilled off under reduced pressure. The residue was purified by silica gel column chromatography [chloroform/methanol=50/1→10/1] to give 820 mg of 3-tert-butyl 2-ethyl (1S,2R)-1-hydroxy-1,2,3-propanetricarboxylate.

820 mg of the carboxylate was dissolved in 20 ml of toluene and stirred with 1.05 g of N,N'-diisopropyl-O-benzylisourea at 100° C. for 2 hours under heating. After addition of 120 mg acetic acid, the reaction solution was cooled to 0° C., and the insolubles were filtered off and washed with iced toluene. The filtrate and the washing liquid were combined and evaporated under reduced pressure. The residue was purified by silica gel column chromatography [hexane/ethyl acetate=9/1→3/1] to give 837 mg of the title compound as a colorless oily substance.

(3) Preparation of 1-benzyl 3-tert-butyl 2-ethyl 1-oxo-1,2,3-propanetricarboxylate 1.5 0 g of 1-benzyl 3-tert-butyl 2-ethyl (1S,2R)-1-hydroxy-1,2,3-propanetricarboxylate in 30 ml of chloroform was stirred with 2.35 g of the Dess-Martin reagent (periodinane) at room temperature for 1.5 hours. The reaction solution was poured into a mixture of saturated aqueous sodium hydrogencarbonate and saturated aqueous sodium thiosulfate and extracted with ethyl acetate. The organic layer was washed with saturated aqueous sodium chloride and then dried over anhydrous magnesium sulfate. The desiccant was filtered off, and the solvent was distilled off under reduced pressure. The residue was purified by silica gel column chromatography [hexane/ethyl acetate=9/1] to give 1.37 g of the title compound as a colorless oily substance (4) Preparation of 1-benzyl 3-tert-butyl 2-ethyl 1-(methoxymethyloxy)-1-propene-1,2,3-tricarboxylate 992 mg of 1-benzyl 3-tert-butyl 2-ethyl 1-oxo-1,2,3-propanetricarboxylate in 10 ml of dimethylformamide was stirred together with 131 mg of 60% oily sodium hydride at room temperature for 1 hour. After addition of 273 mg of chloromethyl methyl ether, the reaction solution was stirred for another 45 minutes, then poured into water and extracted with ethyl ether. The organic layer was dried over anhydrous magnesium sulfate. The desiccant was filtered off, and the solvent was distilled off under reduced pressure. The residue was purified by silica gel column chromatography [hexane/ethyl acetate=5/1] to give 962 mg of the title compound as a colorless oily substance.

REFERENCE EXAMPLE 6

Preparation of (2RS,3RS)-3-(tert-butoxycarbonyl)-5-oxotetrahydrofuran-2-carboxylic acid (1) Preparation of (2RS,3SR)-2-(benzyloxycarbonyl)-5-oxotetrahydrofuran-3-carboxylic acid 5.2 g of (2RS,3SR)-5-oxotetrahydrofuran-2,3-dicarboxylic acid in 88 ml of acetone was stirred with 6.5 g of 1,1'-dicyclohexylcarbodiimide at room temperature for 2 hours. After addition of 3.26 ml of benzyl alcohol, the reaction solution was stirred at the same temperature for 12 hours. The insolubles were filtered off, and the filtrated was concentrated under reduced pressure. The residue was purified by silica gel column chromatography [hexane/ethyl acetate=4/1→chloroform/methanol=50/1] to give 7.93 g of the title compound as a yellow solid.

(2) Preparation of 2-benzyl 3-tert-butyl (2RS,3RS)-5-oxotetrahydrofuran-2,3-dicarboxylate 7.93 g of (2RS,3SR)-2-(benzyloxycarbonyl)-5-oxotetrahydrofuran-3-carboxylic acid in 75 ml of chloroform was mixed with 5.5 g of 4-dimethylaminopyridine, 8.6 g of 1-ethyl-3-(3-dimethylaminopropyl)carbodiimide hydrochloride and 5.7 ml of tert-butyl alcohol successively and stirred at room temperature for 60 hours. The reaction solution was poured into 1N hydrochloric acid under cooling with ice and extracted with ethyl acetate. The organic layer was dried over anhydrous magnesium sulfate. The desiccant was filtered off, and the solvent was distilled off under reduced pressure. The residue was purified by silica gel column chromatography [hexane/ethyl acetate=5/1] to give 6.48 g of the title compound as a white solid.

(3) Preparation of (2RS,3RS)-(3-tert-butoxycarbonyl)-5-oxotetrahydrofuran-2-carboxylic acid 4.92 g of 2-benzyl 3-tert-butyl (2RS,3RS)-5-oxotetrahydrofuran-2,3-dicarboxylate in 50 ml of ethyl acetate was catalytically reduced with 500 mg of a 10% palladium-carbon catalyst at room temperature for 3 hours under atmospheric pressure of hydrogen. The catalyst was filtered off, and the filtrate was evaporated to dryness to give 3.44 g of the title compound as a white solid.

REFERENCE EXAMPLE 7

Preparation of (2S,3S)-3-(tert-butoxycarbonyl)-5-oxotetrahydrofuran-2-carboxylic acid (1) Preparation of (2S,3R)-5-oxotetrahydrofuran-2,3-dicarboxylic acid 16.49 g of 3-tert-butyl 1,2-diethyl (1S,2R)-1-hydroxy-1,2,3-propanetricarboxylate prepared in Reference Example 5(1), 100 ml of acetic acid and 50 ml of concentrated hydrochloric acid were mixed and stirred at 70° C. for 5 hours. The acetic acid and the hydrochloric acid were distilled off under reduced pressure, and the residue was dissolved in 100 ml of acetic acid and 50 ml of concentrated hydrochloric acid again and stirred at 70° C. for 12 hours. The acetic acid and the hydrochloric acid were distilled off under reduced pressure, and the residue was mixed with 100 ml of trifluoroacetic acid and stirred at 60° C. for 5 hours. The trifluoroacetic acid was distilled off under reduced pressure, and the residue was crystallized from hexane-ethyl acetate to give 9.38 g of the title compound as a white powder.

(2) Preparation of (2S,3S)-3-(tert-butoxycarbonyl)-5-oxotetrahydrofuran-2-carboxylic acid The title compound was prepared in the same manner as in Reference Example 6 by using (2R,3R)-5-oxotetrahydrofuran-2,3-dicarboxylic acid as the starting material.

INDUSTRIAL APPLICABILITY

The compound of the present invention has excellent protein-farnesyl transferase (PET) inhibitory activities and is useful as an antitimor agent or an anti-HIV agent.

We claim:
1. A compound represented by general formula (I) or a pharmaceutically acceptable salt or ester thereof:

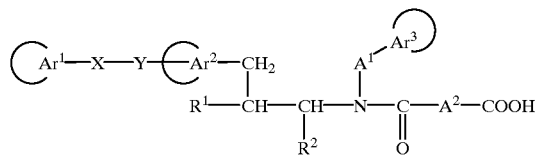

wherein each of

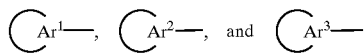

which may be the same or different, is an aryl group or an aromatic heterocyclic group which may have substituent(s) selected from the group consisting of a halogen atom, a hydroxyl group, an amino group, a nitro group, a cyano group, a carboxyl group, a lower alkyl group, a lower alkenyl group, a lower alkoxy group, a lower hydroxyalkyl group, a lower fluoroalkyl group, a lower alkoxycarbonyl group, a carbamoyl group and a lower alkylcarbamoyl group; $A^1$ is a $C_{1-6}$ chain hydrocarbon group which may have substituent(s) selected from the group consisting of a halogen atom, a lower alkyl group, an oxo group, a lower hydroxyalkyl group and a lower alkoxy group or a group represented by —$A^{1a}$—$W^1$—$A^{1b}$— wherein $A^{1a}$ is a $C_{1-5}$ chain hydrocarbon group which may have substituent(s) selected from the group consisting of a halogen atom, a lower alkyl group, an oxo group, a lower hydroxyalkyl group and a lower alkoxy group; $A^{1b}$ is a single bond or a $C_{1-4}$ chain hydrocarbon group which may have substituent(s) selected from the group consisting of a halogen atom, a lower alkyl group, an oxo group, a lower hydroxyalkyl group and a lower alkoxy group; $W^1$ is an oxygen atom, a sulfur atom, an ethynylene group, a cyclopropylene group or a group represented by —$NR^w$—; and $R^w$ is a hydrogen atom or a lower alkyl group; $A^2$ is a $C_{1-8}$ chain hydrocarbon group which may have substituent(s) selected from the group consisting of a halogen atom, a lower alkyl group, a hydroxyl group, a lower hydroxyalkyl group, a lower alkoxy group, a carboxyl group, a lower alkoxycarbonyl group, a lower alkenyloxycarbonyl group, a lower carboxyalkyl group, an aryl group and aralkyl group; $R^1$ is a lower alkyl group or a lower alkenyl group which may have substituent(s) selected from the group consisting of a hydroxyl group, a lower alkoxy group, a lower alkoxycarbonyl group, a carbamoyl group, a lower alkylcarbamoyl group and a lower alkylhydrazinocarbonyl group, a lower alkoxy group, a carboxyl group, a lower alkoxycarbonyl group, a carbamoyl group, a lower alkylcarbamoyl group, a group represented by $R^a$COO— wherein $R^a$ is a hydrogen atom, an amino group, a lower alkyl group, a lower alkoxy group or a lower alkylamino group or by $R^b$CONR$^c$— wherein $R^b$ is a hydrogen atom, an amino group, a lower alkyl group, a lower alkoxy group or a lower alkylamino group; and $R^c$ is a hydrogen atom or a lower alkyl group or an alicyclic group which may have substituent(s) selected from the group consisting of a halogen atom, a hydroxyl group, an amino group, a nitro group, a cyano group, a carboxyl group, a lower alkyl group, a lower alkenyl group, a lower alkoxy group, a lower hydroxyalkyl group, a lower fluoroalkyl group, a lower alkoxycarbonyl group, a carbamoyl group and a lower alkyl carbamoyl group and may have one or two oxygen atoms and/or one or two nitrogen atoms; $R^2$ is a lower alkyl group; and each of X and Y which may be the same or different, is an oxygen atom, a sulfur atom, a carbonyl group, a group represented by —CHR$^d$— wherein R$^d$ is a hydrogen atom or a lower alkyl group or by —NR$^e$— wherein R$^e$ is a hydrogen atom or a lower alkyl group, or X and Y together represent a vinylene group or an ethynylene group, provided that when one of X and Y is an oxygen atom, a sulfur atom or a group represented by —NR$^e$— wherein R$^e$ is the same as defined above, the other is a carbonyl group or a group represented by —CHR$^d$— wherein R$^d$ is the same defined above.

2. The compound according to claim 1, wherein

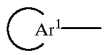

is a phenyl group or a thienyl group.

3. The compound according to claim 1, wherein

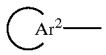

is a phenyl group, a thienyl group, a furyl group, a thiazolyl group, an oxazolyl group, an isoxazolyl group a pyridyl group or a pyrimidinyl group.

4. The compound according to claim 1, wherein

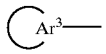

is a phenyl group, a thienyl group, a naphthyl group, a benzothienyl group or a benzofuranyl group.

5. The compound according to claim 1, wherein $A^2$ is a group represented by —$CH_2$—, —$CH_2CH_2CH_2$—, —$CH_2CH=CH$, —$CH_2CH_2O$— or —$CH_2C\equiv C$—.

6. The compound according to claim 1, wherein $A^1$ is a group represented by formula (a):

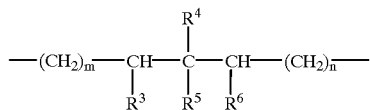

[a]

wherein $R^3$ is a hydrogen atom, a hydroxyl group, a lower hydroxyalkyl group, a lower alkoxy group or a carboxyl group; $R^4$ is a hydrogen atom, a halogen atom, a hydroxyl group, a lower alkoxy group, a carboxyl group or a lower carboxyalkyl group; $R^5$ is a hydrogen atom, a lower hydroxyalkyl group, a carboxyl group, a lower alkoxycarbonyl group or a lower alkenyloxycarbonyl group; $R^6$ is a hydrogen atom, a halogen atom, a hydroxyl group or a carboxyl group; each of m and n which may be the same different, is an integer of from 0 to 2.

7. The compound according to claim 1, wherein $A^2$ is a group represented by formula (b):

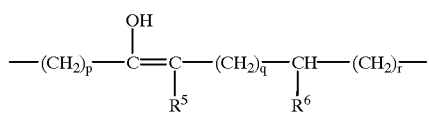

[b]

wherein $R^5$ is a hydrogen atom, a lower hydroxyalkyl group, a carboxyl group, a lower alkoxycarbonyl group or a lower alkenyloxycarbonyl group; $R^6$ is a hydrogen atom, a hydroxyl group or a carboxyl group; p is 0 or 1; and each of q and r which may be the same or different, is an integer of from 0 to 2.

8. The compound according to claim 1, wherein $R^1$ is a lower alkoxycarbonyl group.

9. The compound according to claim 1, wherein X is a group represented by —$NR^e$— wherein $R^e$ is a hydrogen atom or a lower alkyl group, and Y is a carbonyl group.

10. The compound according to claim 1, wherein X is an oxygen atom, and Y is a group represented by —$CHR^d$— wherein $R^d$ is a hydrogen atom or a lower alkyl group.

11. The compound according to claim 1, wherein X is —$CHR^d$— wherein $R^d$ is a hydrogen atom or a lower alkyl group, and Y is an oxygen atom.

12. The compound according to claim 1, wherein both X and Y are groups represented by —$CHR^d$— wherein $R^d$ is a hydrogen atom or a lower alkyl group.

13. The compound according to claim 1, wherein X and Y together represent a vinylene group.

14. An antitumor agent comprising a compound represented by general formula (I) or a pharmaceutically acceptable salt or ester thereof:

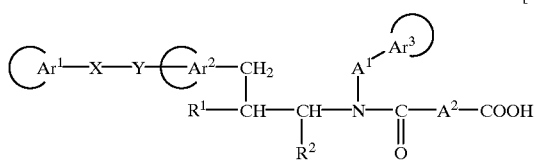

[I]

wherein each of

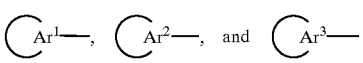

which may be the same or different, is an aryl group or an aromatic heterocyclic group which may have substituent(s) selected from the group consisting of a halogen atom, a hydroxyl group, an amino group, a nitro group, a cyano group, a carboxyl group, a lower alkyl group, a lower alkenyl group, a lower alkoxy group, a lower hydroxyalkyl group, a lower fluoroalkyl group, a lower alkoxycarbonyl group, a carbamoyl group and a lower alkylcarbamoyl group; $A^1$ is a $C_{1-6}$ chain hydrocarbon group which may have substituent(s) selected from the group consisting of a halogen atom, a lower alkyl group, an oxo group, a lower hydroxyalkyl group and a lower alkoxy group or a group represented by —$A^{1a}$—$W^1$—$A^{1b}$— wherein $A^{1a}$ is a $C_{1-5}$ chain hydrocarbon group which may have substituent(s) selected from the group consisting of a halogen atom, a lower alkyl group, an oxo group, a lower hydroxyalkyl group and a lower alkoxy group; $A^{1b}$ is a single bond or a $C_{1-4}$ chain hydrocarbon group which may have substituent(s) selected from the group consisting of a halogen atom, a lower alkyl group, an oxo group, a lower hydroxyalkyl group and a lower alkoxy group; $W^1$ is an oxygen atom, a sulfur atom, an ethynylene group, a cyclopropylene group or a group represented by —$NR^w$—; and $R^2$ is a hydrogen atom or a lower alkyl group; $A^2$ is a $C_{1-8}$ chain hydrocarbon group which may have substituent(s) selected from the group consisting of a halogen atom, a lower alkyl group, a hydroxyl group, a lower hydroxyalkyl group, a lower alkoxy group, a carboxyl group, a lower alkoxycarbonyl group, a lower alkenyloxycarbonyl group, a lower carboxyalkyl group, an aryl group and aralkyl group; $R^1$ is a lower alkyl group or a lower alkenyl group which may have substituent(s) selected from the group consisting of a hydroxyl group, a lower alkoxy group, a lower alkoxycarbonyl group, a carbamoyl group, a lower alkylcarbamoyl group and a lower alkylhydrazinocarbonyl group, a lower alkoxy group, a carboxyl group, a lower alkoxycarbonyl group, a carbamoyl group, a lower alkylcarbamoyl group, a group represented by $R^a$COO— wherein $R^a$ is a hydrogen atom, an amino group, a lower alkyl group, a lower alkoxy group or a lower alkylamino group or by $R^bCONR^c$— wherein $R^b$ is a hydrogen atom, an amino group, a lower alkyl group, a lower alkoxy group or a lower alkylamino group; and $R^c$ is a hydrogen atom or a lower alkyl group or an alicyclic group which may have substituent(s) selected from the group consisting of a halogen atom, a hydroxyl group, an amino group, a nitro group, a cyano group, a carboxyl group, a lower alkyl group, a lower alkenyl group, a lower alkoxy group, a lower hydroxyalkyl group, a lower fluoroalkyl group, a lower alkoxycarbonyl group, a carbamoyl group and a lower alkylcarbamoyl group and may have one or two oxygen atoms and/or one or two nitrogen atoms; $R^2$ is a lower alkyl group; and each of X and Y which may be the same or different, is an oxygen atom, a sulfur atom, a carbonyl group, a group represented by —$CHR^d$— wherein $R^d$ is a hydrogen atom or a lower alkyl group or by —$NR^e$— wherein $R^e$ is a hydrogen atom or a lower alkyl group, or X and Y together represent a vinylene group or an ethynylene group, provided that when one of X and Y is an oxygen atom, a sulfur atom or group represented by —$NR^e$— wherein $R^e$ is the same as defined above, the other is a carbonyl group or a group represented by —$CHR^d$— wherein $R^d$ is the same defined above, as an active ingredient.

* * * * *